US008788217B2

(12) United States Patent
Feingold et al.

(10) Patent No.: US 8,788,217 B2
(45) **Date of Patent: *Jul. 22, 2014**

(54) INFORMATION NOTIFICATION SAMPLE PROCESSING SYSTEM AND METHODS OF BIOLOGICAL SLIDE PROCESSING

(71) Applicant: DAKO Denmark A/S, Glostrup (DK)

(72) Inventors: Gordon Feingold, Santa Barbara, CA (US); Marc Key, Ojai, CA (US); John Favuzzi, Santa Barbara, CA (US); Rosanne Welcher, Ventura, CA (US)

(73) Assignee: DAKO Denmark A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,949

(22) Filed: Jan. 23, 2013

(65) Prior Publication Data

US 2013/0203103 A1 Aug. 8, 2013

Related U.S. Application Data

(63) Continuation of application No. 13/073,345, filed on Mar. 28, 2011, now Pat. No. 8,386,195, which is a continuation of application No. 12/076,516, filed on Mar. 19, 2008, now Pat. No. 7,937,228, which is a continuation of application No. 10/538,745, filed as application No. PCT/US03/40974 on Dec. 19, 2003, now Pat. No. 7,400,983.

(60) Provisional application No. 60/435,601, filed on Dec. 20, 2002.

(51) Int. Cl.
*G01N 35/00* (2006.01)

(52) U.S. Cl.
USPC .................... 702/32; 422/67; 436/46; 436/49

(58) Field of Classification Search
None
See application file for complete search history.

(56) References Cited

U.S. PATENT DOCUMENTS 3,219,416 A 11/1965 Natelson
3,398,935 A 8/1968 Livesey et al.

(Continued)

FOREIGN PATENT DOCUMENTS

AU 0644876 B2 12/1993
CA 2172363 3/1995

(Continued)

OTHER PUBLICATIONS

U.S. Appl. No. 60/435,601, "Sample Processing System and Methods of Sample Processing," filed Dec. 20, 2002, 81 pages.

(Continued)

*Primary Examiner* — Manuel L Barbee
(74) *Attorney, Agent, or Firm* — Finnegan, Henderson, Farabow, Garrett & Dunner LLP

(57) ABSTRACT

A sample processing system that may be automated and methods are disclosed where samples are arranged on a carrier element and a process operation control system automatically processes the samples perhaps robotically with an operationally-influential exteriorly-consequential information monitor or a data capture element. Significant process details as well as operationally-influential exteriorly-consequential information may be monitored and an automatic notice element may cause notification of a person at some display that may be remote. Various people may be notified, such as an administrator, a supplier, or a manufacturer of an opportunity for some action such as reagent reordering or the like. A simulated motion display may be included to "watch" simulated operation in real time or long after completion of the actual processing.

20 Claims, 11 Drawing Sheets

101 120 140 150 102 110 111 104 112

(56) References Cited

U.S. PATENT DOCUMENTS 3,482,082 A 12/1969 Isreeli
3,513,320 A 5/1970 Weldon
3,547,064 A 12/1970 Glass
3,553,438 A 1/1971 Blitz et al.
3,600,900 A 8/1971 Buddecke
3,644,715 A 2/1972 Holderith
3,660,638 A 5/1972 Oberli
3,680,967 A 8/1972 Englehardt
3,772,154 A 11/1973 Isenberg et al.
3,801,775 A 4/1974 Acker
3,807,851 A 4/1974 Knox et al.
3,831,006 A 8/1974 Chaffin, III et al.
3,851,972 A 12/1974 Smith et al.
3,853,092 A 12/1974 Amos et al.
3,854,703 A 12/1974 Gibbs et al.
3,873,079 A 3/1975 Kuus
3,876,297 A 4/1975 Appeldorn et al.
3,909,203 A 9/1975 Young et al.
RE28,585 E 10/1975 Amos et al.
3,916,157 A 10/1975 Roulette et al.
3,916,160 A 10/1975 Russo et al.
3,971,917 A 7/1976 Maddox et al.
3,976,028 A 8/1976 Howells et al.
3,994,594 A 11/1976 Sandrock et al.
4,013,038 A 3/1977 Rogers et al.
4,018,565 A 4/1977 Fletcher, III et al.
4,039,288 A 8/1977 Moran
4,066,412 A 1/1978 Johnson et al.
4,083,638 A 4/1978 Sandrock et al.
4,084,541 A 4/1978 Ito
4,092,952 A 6/1978 Wilkie et al.
4,100,309 A 7/1978 Micklus et al.
4,113,437 A 9/1978 Duff et al.
4,115,861 A 9/1978 Allington
4,133,642 A 1/1979 Nosaka et al.
4,135,883 A 1/1979 McNeil et al.
4,139,867 A 2/1979 Foerster
4,159,875 A 7/1979 Hauser
4,163,643 A 8/1979 Hunter et al.
4,200,056 A 4/1980 Johnson
4,200,607 A 4/1980 Suzuki
4,227,810 A 10/1980 Sandrock et al.
4,245,967 A 1/1981 Busselet
4,263,504 A 4/1981 Thomas
4,281,387 A 7/1981 Kraft et al.
4,286,146 A 8/1981 Uno et al.
RE30,730 E 9/1981 Duff
4,298,571 A 11/1981 DiFulvio et al.
4,311,667 A 1/1982 Gocho
4,323,537 A 4/1982 Mody
4,338,279 A 7/1982 Orimo et al.
4,346,056 A 8/1982 Sakurada
4,371,498 A 2/1983 Scordato et al.
4,404,641 A 9/1983 Bazarnik
4,406,547 A 9/1983 Aihara
4,447,395 A 5/1984 Englar et al.
4,455,280 A 6/1984 Shinohara et al.
4,467,073 A 8/1984 Creasy
4,467,603 A 8/1984 Wilson
4,488,679 A 12/1984 Bockholt et al.
4,510,169 A 4/1985 Linner
4,517,160 A 5/1985 Galle et al.
4,528,159 A 7/1985 Liston
4,531,455 A 7/1985 Palmer
4,538,222 A * 8/1985 Crain et al. .................... 700/67
4,539,632 A 9/1985 Hansen et al.
4,558,946 A 12/1985 Galle et al.
4,567,748 A 2/1986 Klass et al.
4,571,699 A 2/1986 Herzog et al.
4,585,622 A 4/1986 Bowe et al.
4,609,017 A 9/1986 Coulter et al.
4,624,588 A 11/1986 Bivin
4,634,576 A 1/1987 Galle et al.
4,634,850 A 1/1987 Pierce et al.
4,643,879 A 2/1987 Hanaway
4,647,432 A 3/1987 Wakatake
4,647,543 A 3/1987 Stöcker
4,656,006 A 4/1987 Assmann et al.
4,664,526 A 5/1987 Scheffler et al.
4,675,299 A 6/1987 Witty et al.
4,678,752 A 7/1987 Thorne et al.
4,678,894 A 7/1987 Shafer
4,680,102 A 7/1987 Ishiwatari
4,681,741 A 7/1987 Hanaway
4,683,120 A 7/1987 Meserol et al.
4,692,308 A 9/1987 Riley et al.
4,692,603 A 9/1987 Brass et al.
4,695,430 A 9/1987 Coville et al.
4,708,886 A 11/1987 Nelson
4,719,087 A 1/1988 Hanaway
4,727,033 A 2/1988 Hijikata et al.
4,728,783 A 3/1988 Brass et al.
4,728,959 A 3/1988 Maloney et al.
4,729,661 A 3/1988 Bell
4,738,824 A 4/1988 Takeuchi
4,751,186 A 6/1988 Baisch et al.
4,754,127 A 6/1988 Brass et al.
4,754,414 A 6/1988 Gocho
4,764,342 A 8/1988 Kelln et al.
4,774,055 A 9/1988 Wakatake et al.
4,781,891 A 11/1988 Galle et al.
4,782,221 A 11/1988 Brass et al.
4,794,239 A 12/1988 Allais
4,795,613 A 1/1989 Azuma et al.
4,795,710 A 1/1989 Muszak et al.
4,797,938 A 1/1989 Will
4,800,762 A 1/1989 Sugaya
4,808,380 A 2/1989 Minekane
4,815,978 A 3/1989 Mazz et al.
4,817,916 A 4/1989 Rawstron
4,824,641 A 4/1989 Williams
4,844,887 A 7/1989 Galle et al.
4,847,208 A 7/1989 Bogen
4,849,177 A 7/1989 Jordan
4,855,109 A 8/1989 Muraishi et al.
4,855,110 A 8/1989 Marker et al.
4,865,811 A 9/1989 Newton et al.
4,868,129 A 9/1989 Gibbons et al.
4,869,114 A 9/1989 Kido et al.
4,871,682 A 10/1989 Mazza
4,873,877 A 10/1989 Harris
4,874,936 A 10/1989 Chandler et al.
4,886,590 A 12/1989 Tittle
4,896,029 A 1/1990 Chandler et al.
4,900,513 A 2/1990 Barker et al.
4,919,887 A 4/1990 Wakatake
4,924,078 A 5/1990 Sant' Anselmo et al.
4,933,147 A 6/1990 Hollar et al.
4,935,875 A 6/1990 Shah et al.
4,939,354 A 7/1990 Priddy et al.
4,939,674 A 7/1990 Price et al.
4,943,415 A 7/1990 Przybylowicz et al.
4,961,906 A 10/1990 Andersen et al.
4,965,049 A 10/1990 Lillig et al.
4,967,606 A 11/1990 Wells et al.
4,985,206 A 1/1991 Bowman et al.
4,986,891 A 1/1991 Sarrine et al.
4,988,482 A 1/1991 Weston
4,998,010 A 3/1991 Chandler et al.
5,031,797 A 7/1991 Boris et al.
5,051,238 A 9/1991 Umetsu et al.
5,053,609 A 10/1991 Priddy et al.
5,059,393 A 10/1991 Quenin et al.
5,068,091 A 11/1991 Toya
5,073,504 A 12/1991 Bogen
5,075,079 A 12/1991 Kerr et al.
5,081,038 A 1/1992 Sugaya et al.
5,102,624 A 4/1992 Muraishi
5,104,527 A 4/1992 Clinkenbeard
5,106,583 A 4/1992 Raysberg et al.
5,118,369 A 6/1992 Shamir
5,122,342 A 6/1992 McCullochh et al.
5,124,536 A 6/1992 Priddy et al.
5,180,606 A 1/1993 Stokes et al.

(56) References Cited

U.S. PATENT DOCUMENTS 5,202,552 A 4/1993 Little et al.
5,225,325 A 7/1993 Miller et al.
5,229,074 A 7/1993 Heath et al.
5,232,664 A 8/1993 Krawzak et al.
5,250,262 A 10/1993 Heidt et al.
5,254,311 A 10/1993 Ushikubo
5,281,395 A 1/1994 Markart et al.
5,282,149 A 1/1994 Grandone et al.
5,289,385 A 2/1994 Grandone
5,311,426 A 5/1994 Donohue et al.
5,316,319 A 5/1994 Suggs
5,316,452 A 5/1994 Bogen et al.
5,316,726 A 5/1994 Babson et al.
5,316,728 A 5/1994 Hayashi et al.
5,322,771 A 6/1994 Rybski et al.
5,331,176 A 7/1994 Sant' Anselmo et al.
5,338,358 A 8/1994 Mizusawa et al.
5,346,672 A 9/1994 Stapleton et al.
5,350,697 A 9/1994 Swope et al.
5,355,304 A 10/1994 DeMoranville et al.
5,355,439 A 10/1994 Bernstein et al.
5,355,695 A 10/1994 Kawaguchi et al.
5,356,595 A 10/1994 Kanamori et al.
5,365,614 A 11/1994 Perkins
5,366,896 A 11/1994 Margrey et al.
5,369,261 A 11/1994 Shamir
5,380,486 A 1/1995 Anami
5,382,511 A 1/1995 Stapleton
5,395,588 A 3/1995 North, Jr. et al.
5,399,316 A 3/1995 Yamada
5,416,029 A 5/1995 Miller et al.
5,417,213 A 5/1995 Prince
5,418,138 A 5/1995 Miller et al.
5,424,036 A 6/1995 Ushikubo
5,425,918 A 6/1995 Healey et al.
5,428,740 A 6/1995 Wood et al.
5,431,455 A 7/1995 Seely
5,432,056 A 7/1995 Hartman et al.
5,439,645 A 8/1995 Saralegui et al.
5,439,649 A 8/1995 Tseung et al.
5,439,826 A 8/1995 Kontorovich
5,446,652 A 8/1995 Peterson et al.
5,449,622 A 9/1995 Yabe et al.
5,473,551 A 12/1995 Sato et al.
5,487,975 A 1/1996 Miller et al.
5,544,650 A 8/1996 Boon et al.
5,549,848 A 8/1996 Zeheb et al.
5,552,087 A 9/1996 Zeheb et al.
5,573,727 A 11/1996 Keefe
5,576,215 A 11/1996 Burns et al.
5,578,452 A 11/1996 Shi et al.
5,595,707 A 1/1997 Copeland et al.
5,602,674 A 2/1997 Weissman et al.
5,612,524 A 3/1997 Sant' Anselmo et al.
5,645,114 A 7/1997 Bogen et al.
5,646,046 A 7/1997 Fischer et al.
5,646,049 A 7/1997 Tayi
5,649,537 A 7/1997 Anelli et al.
5,650,136 A 7/1997 Platzek et al.
5,650,327 A 7/1997 Copeland et al.
5,654,199 A 8/1997 Copeland et al.
5,654,200 A 8/1997 Copeland et al.
5,656,493 A 8/1997 Mullis et al.
5,675,715 A 10/1997 Bernstein et al.
5,677,966 A 10/1997 Doerrer et al.
5,681,543 A 10/1997 Schmitt-Willich et al.
5,695,739 A 12/1997 Schmitt-Willich et al.
5,696,887 A 12/1997 Bernstein et al.
5,723,092 A 3/1998 Babson
5,733,528 A 3/1998 Felder et al.
5,737,449 A 4/1998 Lee
5,737,499 A 4/1998 Bernstein et al.
5,758,033 A 5/1998 Bernstein et al.
5,776,414 A 7/1998 Itani et al.
5,798,092 A 8/1998 Schmitt-Willich et al.
5,820,849 A 10/1998 Schmitt-Willich et al.
5,839,091 A 11/1998 Rhett et al.
5,854,075 A 12/1998 Levine et al.
5,875,286 A 2/1999 Bernstein et al.
5,876,698 A 3/1999 Schmitt-Willich et al.
5,885,529 A 3/1999 Babson et al.
5,888,576 A 3/1999 Nagano
5,888,733 A 3/1999 Hyldig-Nielsen et al.
5,888,876 A 3/1999 Shiozawa et al.
5,896,488 A 4/1999 Jeong
5,930,461 A 7/1999 Bernstein et al.
5,945,341 A 8/1999 Howard, III
5,947,167 A 9/1999 Bogen et al.
5,948,359 A 9/1999 Kalra et al.
5,958,341 A 9/1999 Chu
5,963,368 A 10/1999 Domanik et al.
5,965,454 A 10/1999 Farmilo et al.
5,985,563 A 11/1999 Hyldig-Nielsen et al.
5,994,071 A 11/1999 Ross et al.
6,017,495 A 1/2000 Ljungmann
6,019,945 A 2/2000 Ohishi et al.
6,045,759 A 4/2000 Ford et al.
6,080,363 A 6/2000 Takahashi et al.
6,083,490 A 7/2000 Ellis et al.
6,092,695 A 7/2000 Loeffler
6,093,574 A 7/2000 Druyor-Sanchez et al.
6,096,271 A 8/2000 Bogen et al.
6,097,995 A 8/2000 Tipton et al.
6,104,483 A 8/2000 Sebok et al.
6,110,425 A 8/2000 Gao et al.
6,110,676 A 8/2000 Coull et al.
6,142,292 A 11/2000 Patterson
6,169,169 B1 1/2001 Hyldig-Nielsen et al.
6,180,061 B1 1/2001 Bogen et al.
6,183,693 B1 2/2001 Bogen et al.
6,192,945 B1 2/2001 Ford et al.
6,193,933 B1 2/2001 Sasaki et al.
6,208,771 B1 3/2001 Jared et al.
6,235,476 B1 5/2001 Bergmann et al.
6,244,474 B1 6/2001 Loeffler
6,245,207 B1 6/2001 Yasuda et al.
6,248,590 B1 6/2001 Malachowski
6,281,004 B1 8/2001 Bogen et al.
6,287,772 B1 9/2001 Stefano et al.
6,296,809 B1 10/2001 Richards et al.
6,310,179 B1 10/2001 Batz et al.
6,327,395 B1 12/2001 Hecht et al.
6,335,208 B1 1/2002 Lowry
6,349,264 B1 2/2002 Rhett et al.
6,352,861 B1 3/2002 Copeland et al.
6,358,682 B1 3/2002 Jaffee et al.
6,387,326 B1 5/2002 Edwards et al.
6,388,061 B1 5/2002 Bergmann et al.
6,395,562 B1 5/2002 Hammock et al.
6,403,036 B1 6/2002 Rodgers et al.
6,403,931 B1 6/2002 Showalter et al.
6,405,609 B1 6/2002 Richards et al.
6,408,931 B1 6/2002 Tilak
6,414,133 B1 7/2002 Dietz-Band et al.
6,416,713 B1 7/2002 Ford et al.
6,420,916 B1 7/2002 Freeman
6,426,794 B1 7/2002 Trainoff
6,444,170 B1 9/2002 Heid et al.
6,451,551 B1 9/2002 Zhan et al.
6,472,217 B1 10/2002 Richards et al.
6,495,106 B1 12/2002 Kalra et al.
6,498,037 B1 12/2002 Lewis et al.
6,509,193 B1 1/2003 Tajima
6,520,313 B1 2/2003 Kaarakainen et al.
6,534,008 B1 3/2003 Angros
6,537,818 B2 3/2003 Richards et al.
6,541,261 B1 4/2003 Bogen et al.
6,544,798 B1 4/2003 Christensen et al.
6,548,822 B1 4/2003 Morris et al.
6,582,962 B1 6/2003 Richards et al.
6,594,537 B1 7/2003 Bernstein et al.
6,615,763 B2 9/2003 Edwards et al.
6,632,598 B1 10/2003 Zhang et al.
6,635,225 B1 10/2003 Thiem et al.

(56) References Cited

U.S. PATENT DOCUMENTS 6,699,710 B1 3/2004 Kononen et al.
6,715,870 B2 4/2004 Kiene et al.
6,735,531 B2 5/2004 Rhett et al.
6,746,851 B1 6/2004 Tseung et al.
6,800,249 B2 10/2004 de la torre-Bueno
6,821,072 B2 11/2004 Thiem et al.
6,827,901 B2 12/2004 Copeland et al.
6,855,559 B1 2/2005 Christensen et al.
6,890,759 B2 5/2005 Bierre et al.
6,943,029 B2 9/2005 Copeland et al.
6,951,663 B1 10/2005 Edwards et al.
7,135,992 B2 11/2006 Karlsson et al.
7,142,852 B2 11/2006 Tell et al.
7,226,788 B2 6/2007 De La Torre-Bueno
7,303,725 B2 12/2007 Reinhardt et al.
7,378,055 B2 5/2008 Lemme et al.
7,396,508 B1 7/2008 Richards et al.
7,400,983 B2 7/2008 Feingold et al.
7,404,927 B2 7/2008 Lemme et al.
8,386,195 B2 * 2/2013 Feingold et al. ................ 702/31
2001/0006417 A1 7/2001 Modlin et al.
2001/0010936 A1 8/2001 Richards et al.
2001/0037072 A1 11/2001 Virtanen
2001/0044124 A1 11/2001 Bacus
2001/0049114 A1 12/2001 Bacus
2001/0055799 A1 12/2001 Baunoch et al.
2002/0001849 A1 1/2002 Copeland et al.
2002/0009391 A1 1/2002 Marquiss et al.
2002/0019001 A1 2/2002 Light
2002/0072122 A1 6/2002 Copelan et al.
2002/0090730 A1 7/2002 Eckert et al.
2002/0091593 A1 7/2002 Fowler
2002/0098595 A1 7/2002 Lubman et al.
2002/0110494 A1 8/2002 Lemme et al.
2002/0111743 A1 8/2002 Gropp
2002/0114733 A1 8/2002 Copeland et al.
2002/0116132 A1 8/2002 Rhett et al.
2002/0176801 A1 11/2002 Giebeler et al.
2002/0178547 A1 12/2002 Shofner et al.
2002/0182628 A1 12/2002 Dietz-Band et al.
2003/0003537 A1 1/2003 Fisher et al.
2003/0022391 A1 1/2003 Richards et al.
2003/0032048 A1 2/2003 Kim et al.
2003/0043963 A1 3/2003 Yamagami et al.
2003/0059790 A1 3/2003 Jaffee et al.
2003/0087443 A1 5/2003 Pressman et al.
2003/0099573 A1 5/2003 Tseung et al.
2003/0100043 A1 5/2003 Kalra et al.
2003/0119200 A1 6/2003 Taft et al.
2003/0120633 A1 6/2003 Torre-Bueno
2003/0124729 A1 7/2003 Christensen et al.
2003/0162221 A1 8/2003 Bader et al.
2003/0163031 A1 8/2003 Madden et al.
2003/0200111 A1 10/2003 Damji
2003/0215357 A1 11/2003 Malterer et al.
2003/0215936 A1 11/2003 Kallioniemi et al.
2004/0002163 A1 1/2004 Reinhardt et al.
2004/0033163 A1 2/2004 Tseung et al.
2004/0039607 A1 2/2004 Savitz et al.
2004/0100415 A1 5/2004 Veitch et al.
2004/0122708 A1 6/2004 Avinash et al.
2004/0219069 A1 11/2004 Kalra et al.
2004/0220745 A1 11/2004 Hosomi
2004/0253662 A1 12/2004 Heid et al.
2004/0260721 A1 12/2004 Coffin et al.
2004/0265185 A1 12/2004 Kitagawa
2004/0266015 A1 12/2004 Favuzzi et al.
2005/0038676 A1 2/2005 Showalter et al.
2005/0059155 A1 3/2005 Graupner et al.
2005/0064535 A1 3/2005 Favuzzi et al.
2005/0106619 A1 5/2005 Bierre et al.
2005/0124028 A1 6/2005 Windeyer et al.
2005/0159982 A1 7/2005 Showalter et al.
2005/0235542 A1 10/2005 Metzner et al.
2005/0250211 A1 11/2005 Reinhardt et al.
2006/0045806 A1 3/2006 Winther et al.
2006/0046298 A1 3/2006 Key et al.
2006/0063265 A1 3/2006 Welcher et al.
2006/0084088 A1 4/2006 Schultz et al.
2006/0085140 A1 4/2006 Feingold et al.
2006/0088928 A1 4/2006 Sweet et al.
2006/0088940 A1 4/2006 Feingold et al.
2006/0105359 A1 5/2006 Favuzzi et al.
2006/0148063 A1 7/2006 Favuzzi et al.
2006/0153736 A1 7/2006 Kalra et al.
2006/0172426 A1 8/2006 Buchanan et al.
2006/0265133 A1 11/2006 Cocks et al.
2007/0010912 A1 1/2007 Feingold et al.
2007/0196909 A1 8/2007 Showalter et al.

FOREIGN PATENT DOCUMENTS

DE 4313807 11/1993
DE 19621179 A1 11/1997
DE 69417908 T2 11/1999
EP 0285851 A2 10/1988
EP 0290018 A2 11/1988
EP 0310303 A1 4/1989
EP 0325101 A1 7/1989
EP 0600939 B1 6/1994
EP 0722363 B1 7/1996
EP 0881481 12/1998
EP 0881481 A1 12/1998
ES 2160486 A1 11/2001
FR 2239167 7/1973
GB 2216259 3/1988
GB 2218514 A 3/2003
JP 54014287 A 2/1979
JP 55107957 8/1980
JP 63240688 A2 10/1988
JP 03209163 A2 12/1991
WO WO 85/03571 8/1985
WO WO 86/02163 A1 4/1986
WO WO 87/00086 1/1987
WO WO 87/00280 A1 1/1987
WO WO 87/06695 A1 11/1987
WO WO 88/02866 4/1988
WO WO 8802865 4/1988
WO WO 89/01616 2/1989
WO WO 91/13335 9/1991
WO WO 92/01919 2/1992
WO WO 92/01919 A1 2/1992
WO WO 93/03451 2/1993
WO WO 93/03451 A1 2/1993
WO WO93/20440 10/1993
WO WO 94/06080 3/1994
WO WO 95/10035 4/1995
WO WO 95/10035 A2 4/1995
WO WO 95/10035 A3 4/1995
WO WO 95/28179 A1 10/1995
WO WO 95/32741 A1 12/1995
WO WO 95/33240 12/1995
WO WO 97/23732 7/1997
WO WO 97/23732 A1 7/1997
WO WO 97/26541 7/1997
WO WO 97/26541 A1 7/1997
WO WO 99/34190 7/1999
WO WO 99/34190 A1 7/1999
WO WO 99/43434 9/1999
WO WO 99/43434 A1 9/1999
WO WO 99/44031 A1 9/1999
WO WO 99/49295 9/1999
WO WO 99/49295 A1 9/1999
WO WO 99/55916 11/1999
WO WO 99/55916 A1 11/1999
WO WO 99/57309 11/1999
WO WO 99/57309 A1 11/1999
WO WO 00/02030 1/2000
WO WO 00/02030 A1 1/2000
WO WO 00/02660 1/2000
WO WO 00/02660 A1 1/2000
WO WO 00/36393 1/2000
WO WO 00/36393 A2 6/2000
WO WO 01/02859 1/2001

(56) References Cited

FOREIGN PATENT DOCUMENTS

| | | |
|---|---|---|
| WO | WO 01/02859 A1 | 1/2001 |
| WO | WO 01/02861 | 1/2001 |
| WO | WO 01/02861 A1 | 1/2001 |
| WO | WO 0106255 A | 1/2001 |
| WO | WO 01/07890 | 2/2001 |
| WO | WO 01/07890 A2 | 2/2001 |
| WO | WO 01/51909 | 7/2001 |
| WO | WO 01/51909 A1 | 7/2001 |
| WO | WO 01/55346 | 8/2001 |
| WO | WO 01/55346 A3 | 8/2001 |
| WO | WO 01/68259 A1 | 9/2001 |
| WO | WO 01/68269 | 9/2001 |
| WO | WO 01/68269 A1 | 9/2001 |
| WO | WO 01/87487 | 11/2001 |
| WO | WO 01/87487 A2 | 11/2001 |
| WO | WO 01/87487 A3 | 11/2001 |
| WO | WO 01/88500 | 11/2001 |
| WO | WO 02/056121 A2 | 7/2002 |
| WO | WO 03/045560 A2 | 6/2003 |
| WO | WO 03/045560 A3 | 6/2003 |
| WO | WO 03/052386 A1 | 6/2003 |
| WO | WO 2004/057307 A1 | 7/2004 |
| WO | WO 2004/057308 A1 | 7/2004 |
| WO | WO 2004/058404 A2 | 7/2004 |
| WO | WO 2004/058404 A3 | 7/2004 |
| WO | WO 2004/058950 A1 | 7/2004 |
| WO | WO 2004/059284 A2 | 7/2004 |
| WO | WO 2004/059284 A3 | 7/2004 |
| WO | WO 2004/059287 A2 | 7/2004 |
| WO | WO 2004/059287 A3 | 7/2004 |
| WO | WO 2004/059288 A2 | 7/2004 |
| WO | WO 2004/059288 A3 | 7/2004 |
| WO | WO 2004/059297 A1 | 7/2004 |
| WO | WO 2004/059441 A2 | 7/2004 |
| WO | WO 2004/059441 A3 | 7/2004 |
| WO | WO 2004/074845 A2 | 9/2004 |
| WO | WO 2004/074847 A1 | 9/2004 |
| WO | WO 2005/031312 | 4/2005 |
| WO | WO 2005/031312 A1 | 4/2005 |
| WO | WO 2005/084263 A2 | 9/2005 |

OTHER PUBLICATIONS

European Patent Application No. 91 90 8695 Supplementary European Search Report, Search completed Mar. 26, 1993, 6 pages.

12 Most Frequently Asked Questions About Thermoelectric Cooling. In: Tellurex Corporation, accessed Oct. 27, 2004, http://www.tellurex.com/12most.html.

Chow et al, "Application of Existing Technology to Meet Increasing Demands for Automated Sample Handling," Clinical Chemistry, 36(9):1 579-1582. 1990.

Dricsoll et al., "Discreet Automated Chemistry System with Tableted Reagents," Clinical Chemistry, 29(9): 1609-1615, 1983.

Garza et al., "Bar Codes in the Clinical Laboratory," Clinical Laboratory Science, 4(1 ):23-24, Jan./Feb. 1991.

Innis et al., "DNA Sequencing with *Themus aquaticus* DNA Polymerase and Direct Sequencing of Polymerase Chain Reaction-Amplified DNA," Proc. Natl. Acad. Sci, 85:9436-9440, Dec. 1988.

International Application No. PCTIUSO3I4O88O Written Opinion dated Sep. 28, 2005.

Lindeman et al., "Evaluation of the Automation of the Immunoenzymatlc Procedures In a Routine Histo/Cytopathalogical Laboratory," Histopathology, 6:739-746, 1982.

Rappaport, "If Bar Code Works in Supermarkets, It Should Be Great for Medicine."Pathologlst, 39(2): 39-40, 185.

Saiki et al., "Enzymatic Amplification of β-Globin Genomic Sequences and Restriction Site Analysis for Diagnosis of Sickle Cell Anemial," Science 230:1350-1353, Dec. 20, 1985.

Stark et al., An automated Devide of Immunocytochemistry, Journal of Immunological Methods, 1986, Elsevier, 107, pp. 89-92.

Tilzer et al., "Use of Bar Code Labels on Collection Tubes for Specimen Management in the Clinical Laboratory." Arch Pathol Lab Mcd, 112:1201-1202, Dec. 1988.

United States nonprovisional Application No. 071488,601, "Automated Biological Reaction Apparatus" filed Mar. 2, 1990.

United States nonprovisional Application No. 071924.052. Automated Biological Reaction Apparatus filed Aug. 31, 1992.

United States District Court, District of Arizona, *Ventana* v. *Cytologix*, CIV 02117 TUC (WDB) Defendant's Surreply in Opposition to Plaintiff's Motion for Preliminary Injunctive Relief filed Jul. 2002.

United States District Court, District of Arizona, *Ventana* v. *Cytologix*, CIV 02117 TUG (RCC) Plaintiff's Motion for Temporary Restraining Order filed Mar. 2002.

United States District Court, District of Arizona, *Ventana* v. *Cytologix*, CIV 02117 TUG (RCC) Plaintiff's Memorandum in Support of Petition for Temporary Restraining Order and Permanent Injunction filed Mar. 2002.

United States District Court, District of Arizona, *Ventana* v. *Cytologix*, CIV 02117 TUC (WDB) Ventana's Reply in Support of its Motion for Preliminary Relief filed Jun. 2002.

United States District Court, District of Arizona, CV03-92 TUC-RCC, *Ventana Medical* vs *Biogenix Laboratories*, Order and Opinion on Motion, Aug. 23, 2005.

United States District Court, District of Arizona, CV03-92 TUC-RCC, *Ventana Medical* vs *Biogenix Laboratories* Reporter's Transcript of Proceedings (Markman Hearing) before Honorable Raner C. Collins, Aug. 11, 2005.

United States District Court, District of Arizona, CV03-92 TUC-RCC. *Ventana Medical* vs *Biogenix Laboratories*, Order filed Oct. 4, 2005.

United States District Court, District of Arizona, CV03-92 TUC-RCC, *Ventana Medical* vs *Biogenix Laboratories*, Judgment in a CMI Case, Oct. 19, 2005.

United States District Court, District of Delaware, *Ventana* v. *Dakocytomation California*, CIV041522 (GMS) Order Construing the Terms of U.S. Patent No. 6,827901 dated Dec. 13, 2005.

United States District Court, Eastern District of Massachusetts, *Vision Biosystems* (*USA*) *Trading* v. *Ventana Medical Systems*, CIV 03CV10391GAO, Defendant's Statement of Undisputed Material Facts, in Support of its Cross-Motion for Summary Judgment of Infringement of the 861 Patent filed Jan. 2004.

United States District Court, Eastern District of Massachusetts, *Vision Biosystems* (*USA*) *Trading* v. *Ventana Medical Systems*, CIV 03CV103910A0, Defendant's Memorandum in Opposition to Plaintiff's Motion for Summary Judgment of No Infringement, and in Support of Defendant's Cross-Motion for Summary Judgment of Infringement of the 861 Patent, filed Jan. 15, 2004.

United States District Court, District of Massachusetts, *Vision Biosystems* (*USA*) *Trading* v. *Ventana Medical Systems*, CIV 03CVIO391GAO, Defendant's Statement of Material Facts in Dispute, in Opposition to Plaintiff's Motion for Summary Judgment o No Infringement of the 861 Patent, filed Jan. 15, 2004.

United States District Court, District of Massachusetts, *Vision Biosystems* (*USA*) *Trading* v. *Ventana Medical Systems*, CIV 03CV10391GAO, Memorandum and Order filed Sep. 30, 2004.

United States District Court, District of Massachusetts, *Vision Biosystems* (*USA*) *Trading* v. *Ventana Medical Systems*, CIV 03CV10391GAO, Plaintiff's motion for Summary Judgment of Non-Infringement Based on Collateral Estoppel filed Oct. 7, 2005.

United States District Court, District of Massachusetts, *Vision Biosystems* (*USA*) *Trading* v. *Ventana Medical Systems*, CIV 03CV10391GAO, Plaintiff's Statement of Undisputed Facts in Support of its Motion for Summary Judgment of Non-Infringement Based on Collateral Estoppel, filed Oct. 7, 2005.

United States District Court, District of Massachusetts, *Vision Biosystems* (*USA*) *Trading* v. *Ventana Medical Systems*, CIV 03CV10391GAO, Plaintiff's Memorandum in Support of its Motion for Summary Judgment of Non-Infringement Based on Collateral Estoppel, filed Oct. 7, 2005.

United States District Court. District of Massachusetts, *Vision Biosystems* (*USA*) *Trading* v. *Ventana Medical Systems*, CIV 03CV10391GAO, Declaration of Richard Wydeven in Support of Plaintiff's Motion for Summary Judgment of Non-Infringement Based on Collateral Estoppel, filed Oct. 7, 2005.

(56) References Cited

OTHER PUBLICATIONS

United States District Court. District of Massachusetts, *Vision Biosystems (USA) Trading* v. *Ventana Medical Systems*, CIV 03CV10391 GAO, Defendant Ventana Medical Systems, Inc.'s Memorandum in Opposition to Vision's Motion for Summary Judgment of Non-Infringement Based on Collateral Estoppel. filed Oct. 21, 2005.
United States District Court, District of Massachusetts, *Vision Biosystems (USA) Trading* v. *Ventana Medical Systems*, CIV 03CV10391 GAO, Defendant Ventena Medical Systems, Inc.'s Statement of Material Facts in Dispute, in Opposition to Vision's Motion for Summar Judgment of Non-Infringement Based on Collateral Estoppel, filed Oct. 21, 2005.
International Preliminary Examination Report, P142WO01, International Application No. PCT/US03/40519 filed Dec. 19, 2003.
International Preliminary Examination Report, P143WO01, International Application No. PCT/US03/40591 filed Dec. 19, 2003.
International Preliminary Examination Report, P131 WO01, International Application No. PCT/US03/40518 filed Dec. 19, 2003.
International Preliminary Examination Report, P139WO01, International Application No. PCT/US03/40880 filed Dec. 22, 2003.
International Preliminary Examination Report, P140WO01, International Application No. PCT/US03/00877 filed Dec. 15, 2003.
International Preliminary Examination Report, P144WO01, International Application No. PCT/US03/41022 filed Dec. 22, 2003.
International Preliminary Examination Report, P1 45W001, International Application No. PCT/US03/40520 filed Dec. 19, 2003, mailing date Mar. 27, 2006.
Written Opinion, P145WO01 • International Application No. PCT/US03/40520 filed Dec. 19, 2003.
International Preliminary Examination Report, P145WO01, International Application No. PCT/US03/40520 filed Dec. 19, 2003, mailing date May 31, 2005.
Written Opinion, P149WO01, International Application No. PCT/US03/40974 filed Dec. 19, 2003.
International Preliminary Examination Report. P1 49W001 • International Application No. PCT/US03/40974 filed Dec. 19, 2003.
U.S. Appl. No. 11/119,417, filed Apr. 30, 2005, Method and Apparatus for Pretreatment of Biological Samples.
Taylor, C., Creating a bar code chemistry system, Medical Laboratory Observer, Feb. 1993;25(2):34-6.
Singer, R. et al, Selection and evaluation of laboratory instrumentation in clinical chemistry: II Guidelines for selection and evaluation, Med Lab Sci. Jan. 1987;44(1):6-14.
Rocks, B. F. et at., Automatic analysers in clinical biochemistry, B F Rocks et al 1986 Clin. Phys. Physiol. Meas. 7 1-29.
Pearson, L. S., The use of bar coding technology, Medical Device Technology, Mar. 1994.
Lifshitz, M. 8, et al., Talking about Technology, Clinical Laboratory Management Review, Jan.-Feb. 1989;3(1):53-4.
U.S. Appl. No. 60/487,998, An Interface Point Server, filed Jul. 17, 2003. 52 pages.
U.S. Appl. No. 10/054,535. Entitled Automated Biological Reaction Apparatus, now Patent No. 6.943,029.
Juroshek et al., A High-Power Automatic Network Analyzer for Measuring the RF Power Absorbed by Biological Samples in a TEM Cell, 1984, IEEE, gpo 818-824.
Meldrum et al., ACAPELLA, a capillary-based submicroliter automated sample preparation system for genome analysis, 1999, IEEE, p. 39-48.
Shepard, DNA purification robotics system, 1994, IEEE, gpo 424-425.
Suckau et al., Automation of MALDI-TOF Analysis for Proteomics, 1999, IEEE, p. 1-5.
Histologic, Technical Bulletin for Histotechnology, 2001, Internet, p. 21-44.
Garrett et al., Successful techniques for supporting multidisciplinary science programs with 'ROPOS: 1999, IEEE, p. 753-756.
Office Action dated Mar. 18, 2010 issued in U.S. Appl. No. 10/538,964, filed Jun. 14, 2005, Sweet et al.
Office Action dated Apr. 15, 2010, issued in U.S. Appl. No. 10/539,561, filed Jun. 16, 2005, Key et al.

* cited by examiner

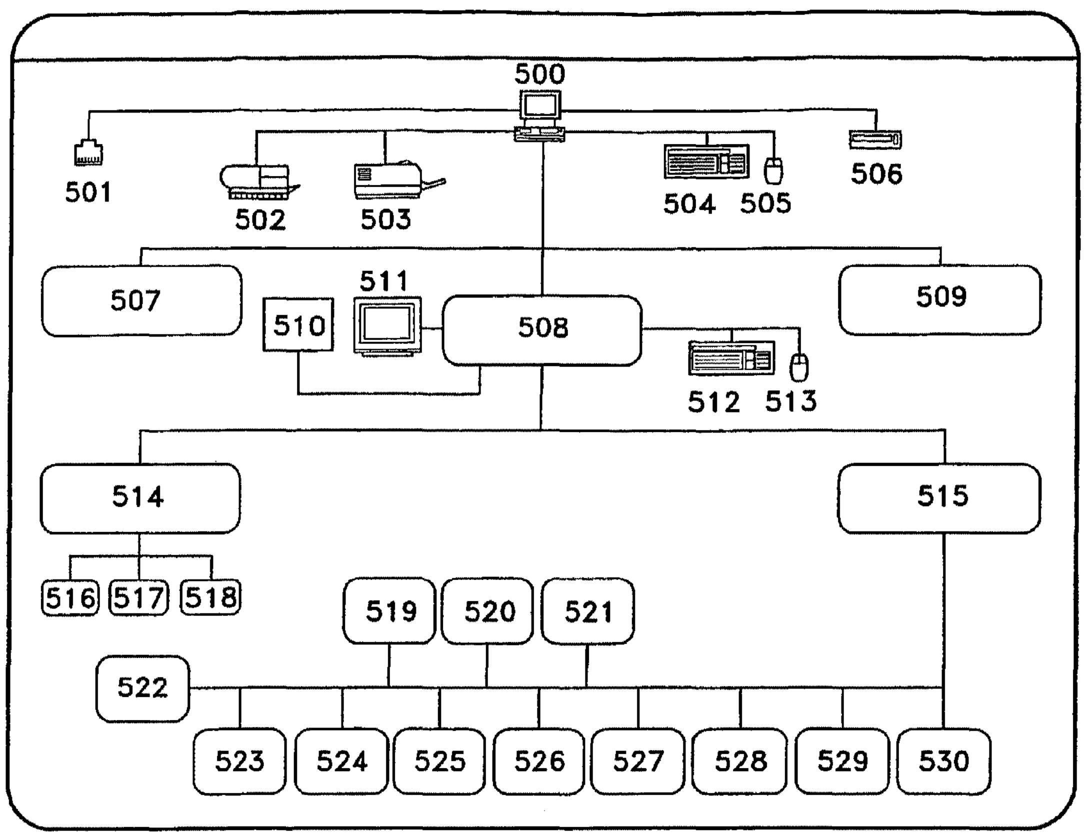

Key to Figure 5

| | |
|---|---|
| 500 Manager | 516 X–Axis |
| 501 100 BaseT | 517 Y–Axis |
| 502 Laser printer | 518 Z–Axis |
| 503 Data Matrix Label Printer | 519 LCD Touch |
| 504 Keyboard | 520 Probe Wash/Swap |
| 505 Mouse | 521 Misc PCBA |
| 506 Storage Media | 522 Cart PCBA |
| 507 Stainer A Embedded PC | 523 Drawer 1 Control |
| 508 Stainer B Embedded PC | 524 Drawer 2 Control |
| 509 Stainer C Embedded PC | 525 Drawer 3 Control |
| 510 Touch Screen | 526 Drawer 4 Control |
| 511 Monitor | 527 Drawer 5 Control |
| 512 Keyboard | 528 Drawer 6 Control |
| 513 Mouse | 529 Drawer 7 Control |
| 514 Motor Controller | 530 Drawer 8 Control |
| 515 Master PCBA | |

Fig. 5

IHC Deparaffinization Process:

| Process | Protocol Step | Time (min) | Temp C | Waste Segregation |
|---|---|---|---|---|
| Deparaffinization | Switch | | | Hazardous Waste |
| | Histoclear | 5 | | |
| | Drain | | | |
| | Histoclear | 5 | | |
| | Drain | | | |
| Re-Hydration | 100% Ethanol | 5 | | |
| | Drain | | | |
| | 100% Ethanol | 5 | | |
| | Drain | | | |
| | 95% Ethanol | 5 | | |
| | Drain | | | |
| | 95% Ethanol | 5 | | |
| | Rinse - Water | 5 | | |
| | Switch | | | Non-Hazardous Waste |
| Target Retrieval | Target Retrieval | 20 | 95 | |
| | Target Retrieval Cool | 20 | 55 | |
| | Rinse - Water | 5 | RT | |
| Enzyme/Antibody Application | Peroxide Block | 5 | | |
| | Enzyme Pretreatment | 5 | | |
| | Rinse - Buffer | | | |
| | Pre-Diluted Antibody | 10 | | |
| | Rinse - Buffer | | | |
| | EnVision-HRP | 10 | | |
| Chromogen/ Counterstain Treatment | Rinse - Buffer | | | |
| | Switch | | | Hazardous Waste |
| | DAB | 5 | | |
| | Rinse - Buffer | | | |
| | Hematoxylin | 5 | | |
| | Rinse - Water | | | |

Fig. 11

INFORMATION NOTIFICATION SAMPLE PROCESSING SYSTEM AND METHODS OF BIOLOGICAL SLIDE PROCESSING

This is a continuation of application Ser. No. 13/073,345, filed Mar. 28, 2011, which is a continuation of application Ser. No. 12/076,516, filed Mar. 19, 2008, which is a continuation of application Ser. No. 10/538,745, filed Jun. 14, 2005, which is a United States National Stage of International Application No. PCT/US2003/040974, filed Dec. 19, 2003, which claims the benefit under 35 U.S.C. §119(e) of U.S. States Provisional Application No. 60/435,601, filed Dec. 20, 2002, all of which are incorporated herein by reference.

TECHNICAL FIELD

This application relates to the field of sample processing systems and methods of automatically monitoring and notifying of certain information for the processing of samples or the process system. The present invention may be directed to the automated processing, treatment, or even staining of samples arranged on carriers, such as slides, and in some embodiments, directed to the continuous or batch processing of samples and carriers. Embodiments may further relate to control systems for sample processing and data input, acquisition, maintenance, and retrieval for sample processing. Applications to which the present invention may especially relate include immunohistochemistry, hybridization, fluorescent in-situ hybridization, special staining, and cytology, as well as potentially other chemical and biological applications.

BACKGROUND

Sample processing in immunohistochemical (LHC) applications and in other chemical and biological analyses may require one or a number of various processing sequences or protocols as part of an analysis of one or more samples. The sample processing sequences or protocols may be defined by the individual or organization requesting an analysis, such as a pathologist or histologist of a hospital, and may be further defined by the dictates of a particular analysis to be performed.

In preparation for sample analysis, a biological sample may be acquired by known sample acquisition techniques and may comprise, for example in IHC applications, tissues generally or even in some applications one or a plurality of isolated cells, such as in microarray samples, and may be presented on a sample carrier including but not limited to microscope slides. Furthermore, the sample may be presented on the carrier variously and potentially in some form of preservation. As one example, a sample such as a layer or slice of skin may be preserved in formaldehyde and presented on a carrier with one or more paraffin or other chemical layers infiltrating the sample.

Immunologic applications, for example, may require processing sequences or protocols that comprise steps such as deparaffinization, target retrieval, reagent application, and staining, especially for in-situ hybridization (ISH) techniques. In some applications, these steps may have been performed manually, potentially creating a time-intensive protocol and necessitating personnel to be actively involved in the sample processing. Even when performed automatically, there have been inefficiencies in such systems. Attempts have been made to automate sample processing to address the need for expedient sample processing and a less manually burdensome operation. However, such previous efforts may have not fully addressed certain specific needs for an automated sample processing system. Previous efforts to automate sample processing may be deficient in several aspects that prevent more robust automated sample processing, such as: the lack of sufficient computer control and monitoring of sample processing; the lack of information sharing for processing protocol and processing status, especially for individual samples; the lack of practical information input and process definition entry capabilities; the lack of diagnostic capabilities; and the lack of real-time or adaptive capabilities for multiple sample batch processing.

Past efforts at automated sample processing for samples presented on carriers such as slides, such as U.S. Pat. No. 6,352,861 to Ventana Medical Systems, Inc. and U.S. Pat. No. 5,839,091 to LabVision Corporation, have not afforded the various advantages and other combinations of features as presented herein.

One of the various aspects that may be significant to users of automated process systems is that of handling information related to the process, the substances used in processing, or even the into the system. The present invention seeks to reduce such effects to some degree and seeks to provide a system that may be considered more user, operator, supplier, or manufacturer friendly.

DISCLOSURE OF INVENTION

The present invention presents an automated sample processing system that may greatly improve operation of automated sample processing from several perspectives. It may act to monitor information existing relative to the sample processing events and materials and may automatically inform those in a position to need to know. It also may capture and store high levels of detail relative to the sample processing events so users, recipients, or even maintenance personnel may have ready and certifiable access to what occurred. As described, sample processing can be accomplished as disclosed herein. In providing this disclosure, it should be understood that the various examples and designs disclosed for sample processing and other disclosed techniques, are not meant to limit the present invention to any particular embodiment, whether apparatus, method, or otherwise. These descriptions are provided rather to describe various sample processing techniques in a manner in which the present invention can be understood. The descriptions incorporated by reference and the various examples should not be construed to limit the present invention to only such techniques. This disclosure, however, may be understood to incorporate the various techniques in the context of the various embodiments of the present invention.

The techniques and systems of sample processing are addressed in a fashion that may provide the processing of one or more samples or of a plurality of groups of one or more samples in sequential or non-sequential fashion. Processing of samples may be determined by the protocol to be followed for each sample or a protocol for multiple samples. Aspects of the present invention may be especially applicable to sample processing having one or a plurality of processing steps to be performed on one, a portion, or an entirety of samples, such protocols identified in some instances by individual carriers presenting the samples or by the individual samples themselves. As mentioned, the present invention may be especially applicable to immunohistochemistry (IHC) techniques, as well as in-situ hybridization (ISH) and fluorescent in-situ hybridization (FISH), special staining of samples, and microarrays; especially techniques incorporating target retrieval or the staining of samples. Furthermore, embodiments may be directed to processing sequences addressing issues of processing control.

Embodiments of the invention may further relate to automated control systems for sample processing. Embodiments may also be directed to data acquisition, input, maintenance, and retrieval for sample processing, as well as information sharing of processing protocol and processing information, and real-time or adaptive capabilities for processing. process instrument itself. In this regard, it has often been considered that operators have to have particular knowledge and skills in order to assure the integrity of the process or instrument or result. Perhaps as a result of this fact, human error was introduced To disclose the foregoing and other objects and in accordance with the purposes of the present invention, as broadly embodied and described herein, the present invention is characterized in various claims and in explanatory disclosure. None of these should be understood as limiting. Further, all claims presented at any time are incorporated in the specification to afford all opportunities of presentation. Claims potentially to be pursued for some of the initially presented aspects of the invention may include any aspects described.

To achieve the foregoing and other objects of invention, and as may be further disclosed and claimed throughout this description, the invention may comprise an automated sample processing system comprising a plurality of drawers, a plurality of sample carrier elements that may even be each removably configured with one of the drawers, and an adaptive or other sample processing control system. The sample carriers may be both movable and removable. The sample processing control system may automate the sample processing system such that one or more samples may be processed according to one or more protocols, potentially indicated by information on slides or otherwise input to the system. This sample processing may comprise one or more sampling protocols and steps, such as deparaffinization, target retrieval, and staining.

A sensor may be provided in some embodiments that may automatically identify information from one or more samples, sample carriers, or slides. In embodiments, protocol information may be provided or made available by the sample processing control system. The sample processing system may then process one or more samples or perhaps slides, or one or more batches of slides, concurrently, sequentially, or in any other temporal fashion, potentially in accordance with protocol information previously provided for a sample by a user or other decision maker. This information can then be made available for use by the sample processing control system. Sample batches or individual slides may even be inserted or removed during processing protocol steps by the control and monitoring accomplished by the adaptive sample processing control system.

Another embodiment of the present invention that may achieve the foregoing and other objects of invention may comprise a method of sample processing, comprising the steps of: accessing at least one of a plurality of samples or sample drawers, providing at least one sample carrier or perhaps a sample carrier retainment assembly configured with at least one sample, configuring at least one of the drawers with the at least one sample carrier, and adaptively processing the sample. The step of processing or perhaps even adaptive processing may be applied to automate the processing of samples and may allow for either or both continuous or batch processing of samples or slides. It may also afford multiple independent sample or slide processing and in some embodiments slide processing to process each slide independently.

Embodiments of the invention may further comprise a method of automated sample processing, comprising the steps of: acquiring or accepting or accessing information such as protocol or reagent information, transmitting such information to at least one sample processing system or even a stand alone processing system, and processing samples. Furthermore, embodiments may provide: for handling, maintaining, sharing, and using the sample processing information. These and other aspects may be provided for individual samples or multiple batch processing, and in a real-time manner. It may also be accomplished in and adaptive manner, perhaps for multiple batch processing or the like.

Again, as mentioned, many of the various aspects of the present invention are applicable to immunohistochemistry (IHC), as well as in-situ hybridization (ISH) and fluorescent in-situ hybridization (FISH), special staining of samples, microarray processes, and techniques incorporating target retrieval or the staining of samples. Furthermore, embodiments are directed to processing sequences addressing issues of processing control, and may be particularly applied to slide processing systems.

BRIEF DESCRIPTION OF THE DRAWINGS

The accompanying figures, are incorporated in and form a part of the description, illustrate some of the preferred embodiments of the present invention. Together with the written description and disclosures of the specification, they serve to explain principles of the invention and to enable each of the disclosed embodiments.

FIG. 5 is a block diagram of an embodiment of the invention.

FIG. 11 is a description of representative deparaffinization steps of an embodiment of the invention.

BEST MODES FOR CARRYING OUT THE INVENTION

The following descriptions are provided to describe various embodiments of the present invention in a manner to facilitate a more detailed understanding some of the inventive features. The variously described examples and preferred embodiments should not be construed to limit the present invention to only the explicitly described systems, techniques, and applications. This description may further be understood to incorporate the various systems, techniques, and applications, both singularly and in various combinations consistent with the various inventive features and embodiments of the present invention. Accordingly, the following is a detailed description of a number of specific embodiments of the invention.

Figure 1:
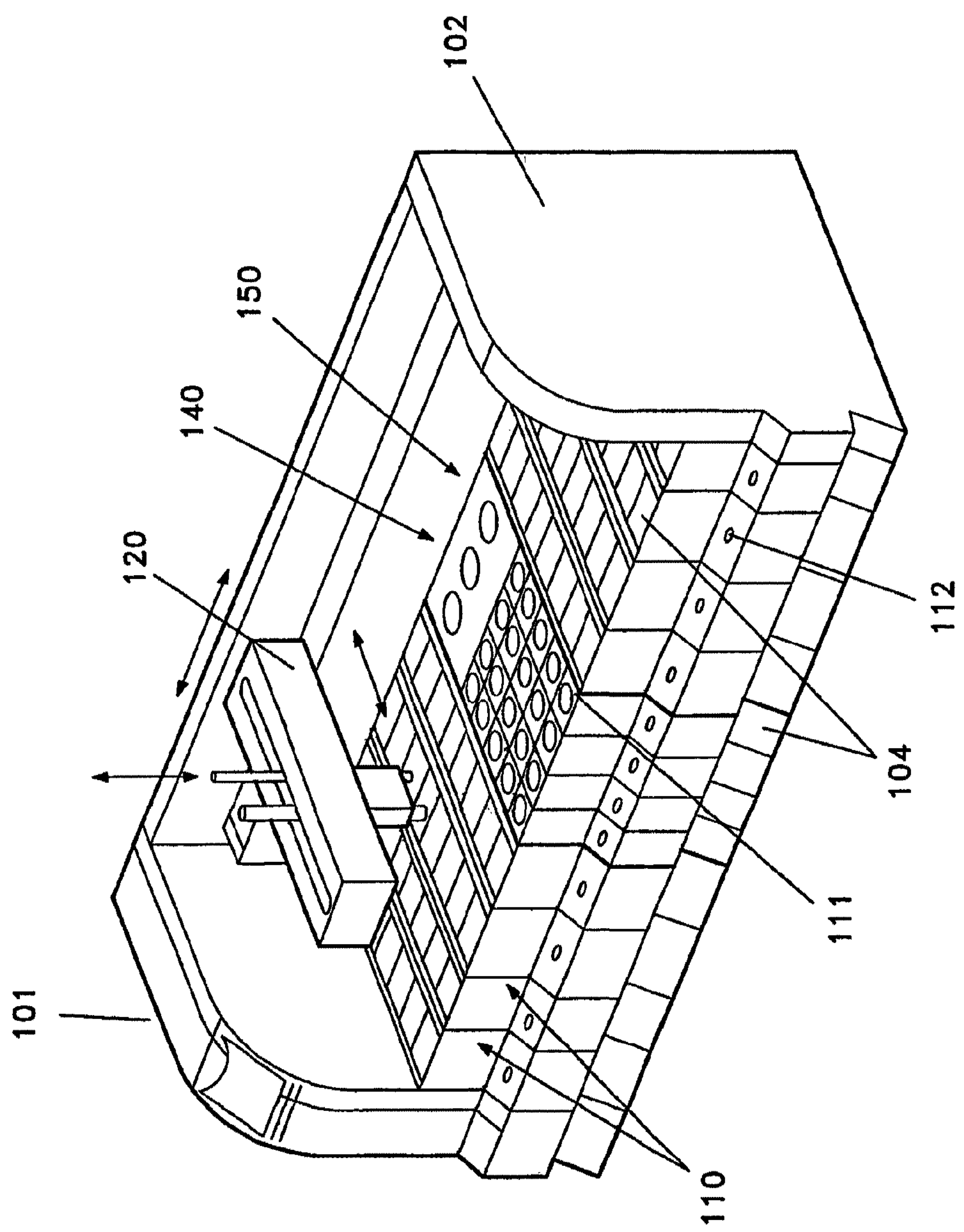
FIG. 1 is a depiction of an embodiment of an overall system incorporating some of the features of the invention.
Figure 10:
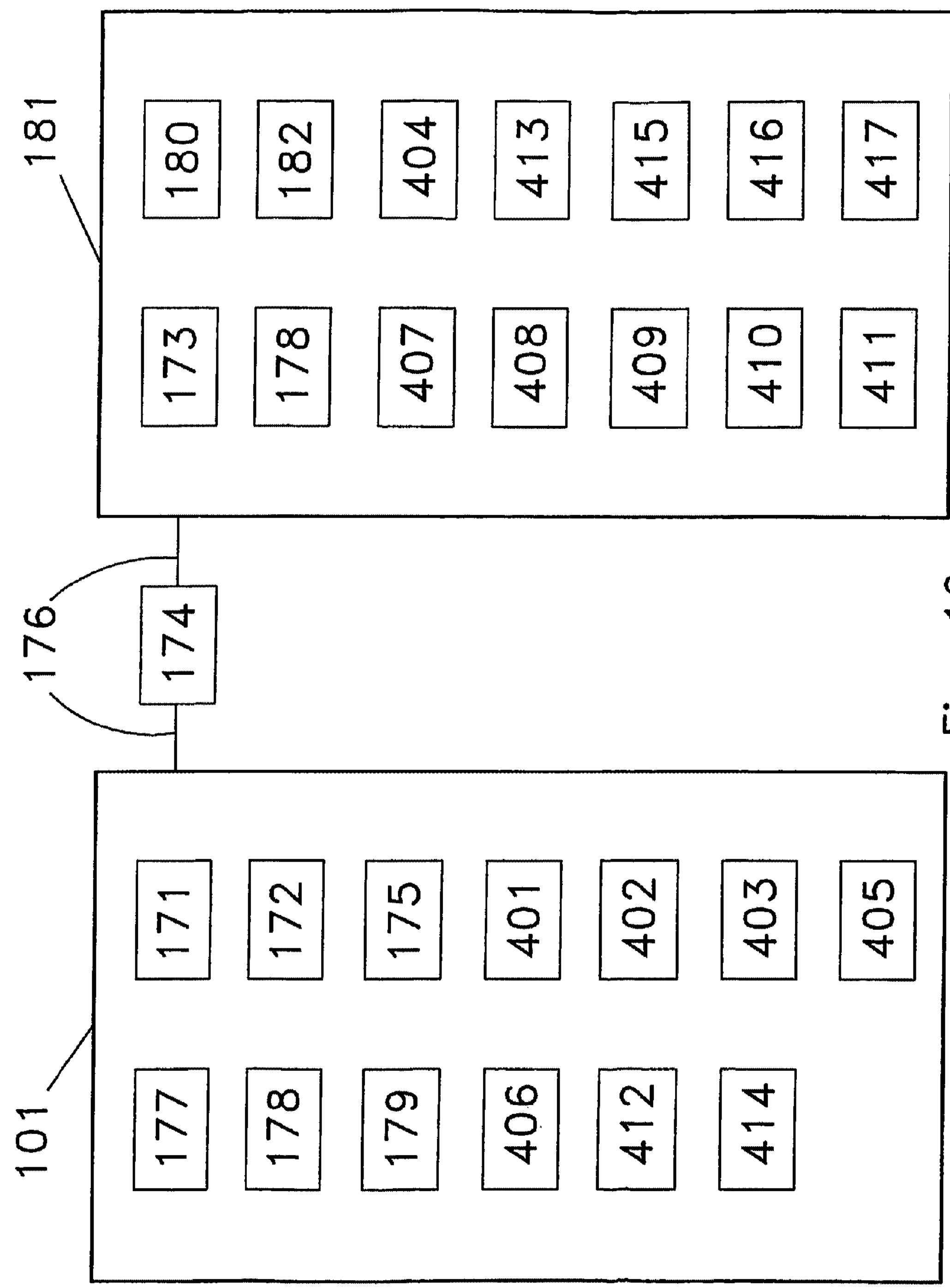
FIG. 10 is a block diagram showing some of the internal software features.

FIG. 1 shows one embodiment of a sample processing system 101 in accordance with the present invention. The sample processing system 101 is configured to achieve an appropriate sequence of events that achieves a desired result to some degree. In achieving this sequence in an automated fashion to some degree the sample processing system is deemed an automated sample processing system and achieves automatic processing of at least one sample. This automated sequence as well as other aspects of the invention may be controlled by hardware, software, or some combination of them to accomplish a desired sequence with limited human intervention. Regardless how achieved, the automated control may be provided by a process operation control system 171 to direct the various activities. As shown in FIG. 10, this (as well as other functionalities discussed) may be software programming or subroutines; again, it may also include hardware or the like. The sample 198 processed may be any material, but is most likely a biologic material such as a biological sample or a biological specimen, perhaps such as a histological sample, e.g. tissue and cell specimens, cells, collections of cells, or tissue samples, the definition to include cell lines, proteins and synthetic peptides, tissues, cell preps, cell preparations, blood, bodily fluids, bone marrow, cytology specimens, blood smears, thin-layer preparations, and micro arrays. It should also be understood to include slide-based biological samples. As used, a sample may be arranged on a carrier element 197 such as a slide, or microscope slide, or the like that may maintain the sample's position or integrity. The carrier element 197 may be configured to move and thus reposition the sample 198. As such, it may be considered a movable carrier element. In processing a slide, the automated sample processing system may serve as an automated slide processing system.

The automated sequence may involve a significant number of steps. In fact each process can itself require many automated movements to achieve its goal. As but one example, the seemingly simple act of merely placing a stain on a sample or a slide can require a surprising number of physical steps. Each of these may involve different valves, motors, switches, relays, or the like. This seemingly simple act can involve:

- beginning X-movement of a robot head;
- moving the robot head an appropriate distance along an X-axis for a probe wash location;
- ending X-movement of the robot head;
- beginning Y-movement of a robot head;
- moving the robot head an appropriate distance along an Y-axis for a probe wash location;
- ending Y-movement of the robot head;
- beginning Z-movement of a robot head;
- lowering a probe tip into a wash area;
- ending Z-movement of the robot head;
- switch a valve to activate a probe wash source;
- open a valve to begin flow of a wash liquid from the probe wash source;
- wash the probe;
- close a valve to end flow of a wash liquid from the probe wash source;
- beginning Z-movement of a robot head;
- raising the probe tip;
- ending Z-movement of the robot head;
- beginning X-movement of a robot head;
- moving a robot head an appropriate distance along an X-axis for a desired stain container;
- ending X-movement of the robot head;
- beginning Y-movement of a robot head;
- moving a robot head an appropriate distance along an Y-axis for a desired stain container;
- ending Y-movement of the robot head;
- beginning Z-movement of a robot head;
- lowering the probe tip over a desired stain container;
- ending Z-movement of the robot head;
- switch a valve to utilize a stain aspiration pressure source;
- open a valve to begin access to the stain aspiration pressure source;
- aspirate stain;
- close a valve to end access to the stain aspiration pressure source;
- beginning Z-movement of a robot head;
- raising the stain containing probe tip;
- ending Z-movement of the robot head;
- beginning X-movement of a robot head;
- moving a robot head an appropriate distance along an X-axis for a particular slide;
- ending X-movement of the robot head;
- beginning Y-movement of a robot head;
- moving a robot head an appropriate distance along an Y-axis for a particular slide;
- ending Y-movement of the robot head;
- beginning Z-movement of a robot head;
- lowering the stain containing probe tip over a particular slide;
- ending Z-movement of the robot head;
- switch a valve to utilize a stain emission pressure source;
- open a valve to begin access to the stain emission pressure source;
- emit stain;
- close a valve to end access to the stain emission pressure source;
- beginning Z-movement of a robot head;
- raising the empty probe tip; and
- ending Z-movement of the robot head.

Each of these type of operations or actions may be relevant to understanding an instrument's operation. Further, each of these types of operations or even a lesser set of significant events may be considered important details of the sample process operation. As explained later, it may be valuable to capture information relative to a significant number of these actions such as all of these operations, some subset of these operations, one-half of these operations, one-third of these operations, or the like. Further, even the nature or type of the events that may be if interest may be varies. In general, any event that may indicate the propriety of operation or processing may be a subject. Naturally in order to achieve automated processing it will be necessary to schedule the various sample process or process operations desired. This can be achieved by an item of software or the like that acts as a multiple event scheduler 401.

A particular design of a system may include cabinet sections 102 that may form outer portions of the system and serve to address general structural considerations of the system (a top cabinet section is not shown in FIG. 1). The sample processing system may also comprise a plurality of drawers 104 used for the handling and processing of samples and sample carriers such as slides, potentially microscope slides. Other sample carriers may be accommodated consistent with the present invention. Each drawer may be configured to accommodate carrier retainment assemblies that hold one or, most likely, a number of the particular carriers, slides, or samples involved.

Figure 2:
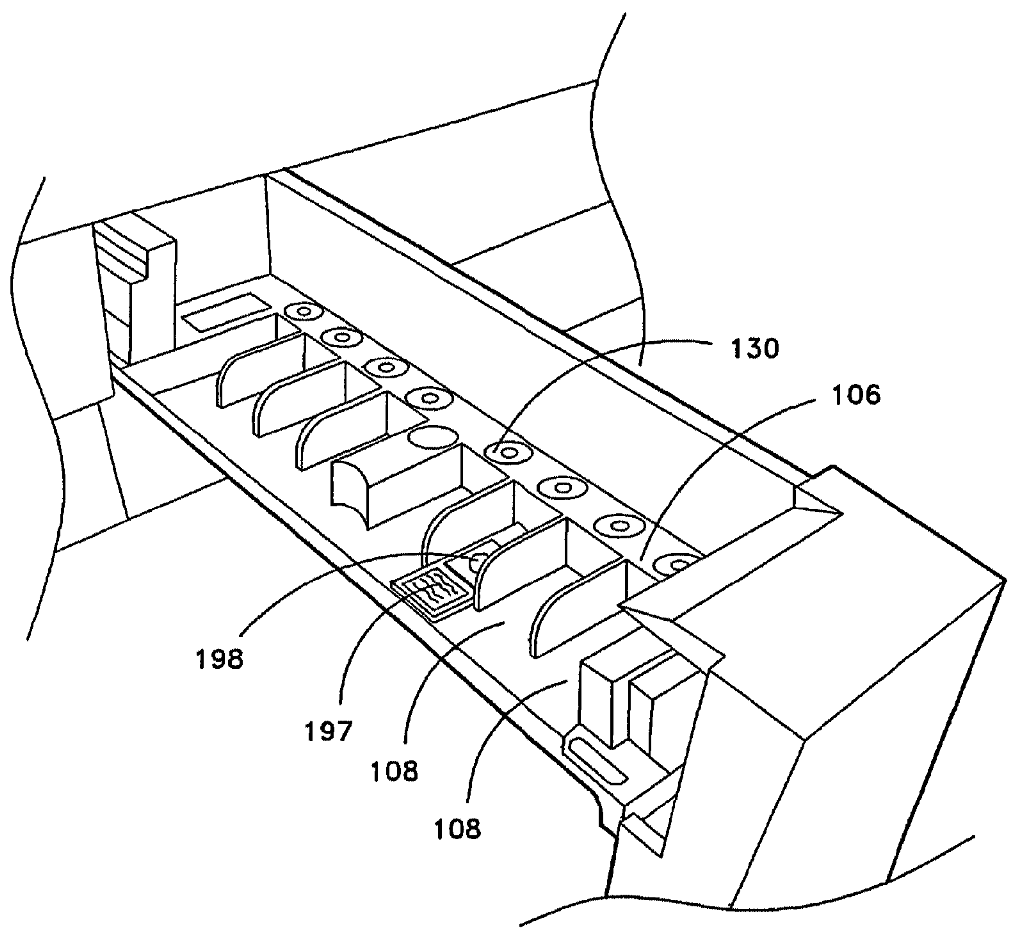
FIG. 2 is a depiction of an embodiment of a portion of a sample carrier assembly of one embodiment of the invention.
Figure 3:
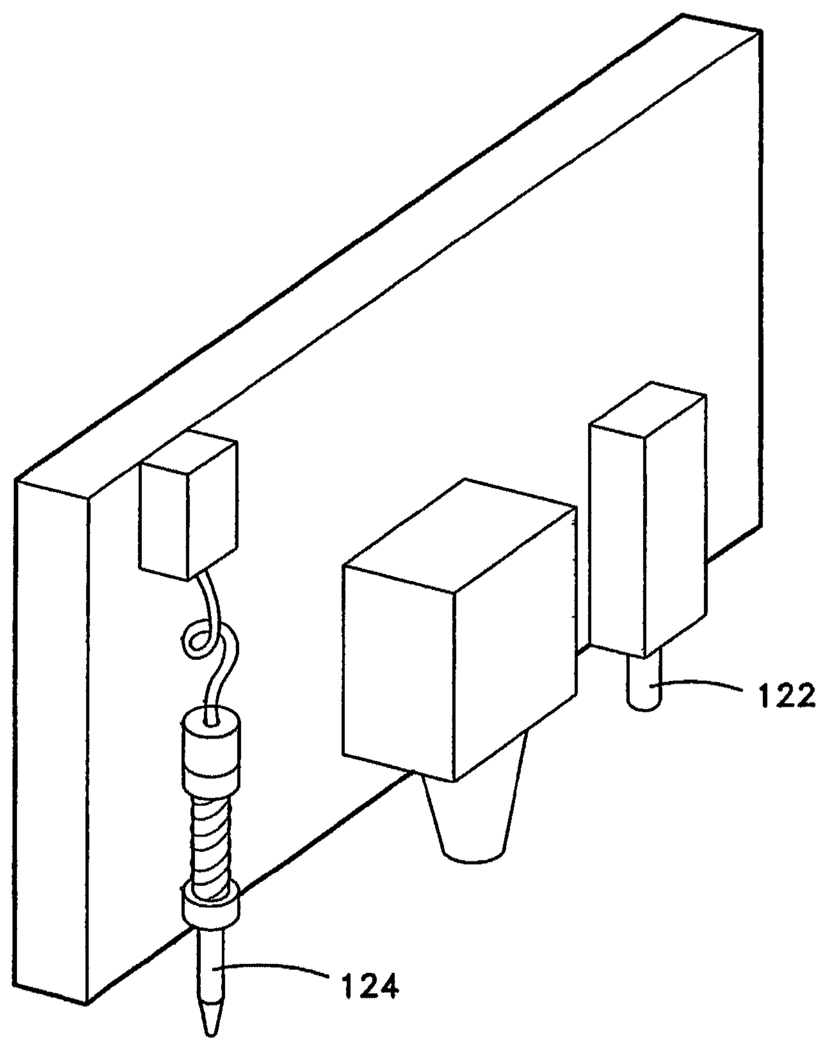
FIG. 3 is a depiction of an embodiment of a robotic movement aspect of one embodiment of the invention.

In holding slides the carrier retainment assembly serves as a slide retainment assembly 106. There may also be carrier racks, modules, or magazines encompassed within each of the two broad terms. As one embodiment of a sample carrier retainment assembly, a slide retainment assembly 106 is shown in FIG. 2. The slide retainment assembly, and indeed the generic carrier retainment assembly may comprise a slide rack, module, or a number of magazines. The slide retainment assembly 106 may be configured to accommodate a plurality of slides in at least one configuration in corresponding sample carrier retention devices 108. The sample carrier retainment assemblies, are utilized in the processing of samples as further described below. It should be further noted that the sample carrier retainment assembly can be removably configured with the drawers 104, and may be stackable or nested within other retainment assemblies.

The general sample processing system 101, and even one or more drawers 110 in the sample processing system 101 may accommodate processing materials such as reagent containers 199 for sample processing, also further described below. A processing material retainment assembly, such as a container rack 111, shown in FIG. 1, may be utilized to accommodate reagent containers 199 or other processing materials within each of drawers 110. Bottle inserts may be preferably configured with the retainment assembly to ensure proper processing material positioning within the processing material retainment assembly and the drawer.

Multiple drawers 104 may be included to allow for one or a plurality of sample processing protocols to be performed by the system 101. Past efforts at sample processing, as previously described, may have been limited to processing sequences for an entire batch of carriers within the system. The present invention, however, in part by providing a plurality of drawers and carrier retainment assemblies, may allow for individual, batch, or multiple batch processing, including real-time or adaptive capabilities, as further described below.

Indicator elements 112 may be provided to indicate a status of the drawers and the carriers or materials within each drawer for an operator of the system. In one embodiment, visual indicators, such as light emitting diodes in preferred embodiments, may be used to indicate if a drawer is available during operation of the sample processing system, and may indicate conditions such as a locked or open condition of a corresponding drawer, carrier capacity status of the drawer or of a carrier retainment assembly within the drawer, and chemical inventory status of the sample processing system, such as reagent loading status or capacity. A warning indication may be given by these or other indicator elements, as well as other indicative signals. One or &plurality of sensors may be utilized to determine the status of the drawer as indicated by the indicator elements 112 and to further provide processing status as further described below.

A processing material unit may be utilized to provide various processing material to the sample processing system 101 and to afford the hazardous and non-hazardous segregation of waste produced during sample processing and the avoidance of cross-contamination. In one embodiment of the present invention, the processing material unit may be configured to accommodate one or a plurality of containers such as deparaffinization solution or other material utilized in sample processing. In some embodiments, the unit may also accommodate waste containers to provide for the collection of waste material from the sample processing. Tubing or other fluid transmission elements may be connected with the containers and the sample processing system 101. Tubing or other fluid transmission elements may also be connected with the waste containers and the system 101.

In accordance with the desire for an automated processing system, embodiments of the present invention may include robotic sample process functions or a robotic motion system 172 responsive to the process operation control system 171 to achieve the desired operation steps. This may further comprise an arm 120 utilized in sample processing, potentially having robotic movement, and in some embodiments, Cartesian movement The arm 120 may comprise, in some preferred embodiments, one or more elements, such as an actuator probe 122, a syringe or probe 124, a sensor element and a non-discrete or other volume fluid and/or air applicator. The actuator probe may be utilized in the configuration and manipulation of the carriers in sample processing, further described below. In some preferred embodiments, the actuator probe 122 configures and manipulates the configuration of slides in the sample carrier retention devices 108 by actuation of carrier adjustment element 130 (see for example FIG. 2), and in some embodiments, by contact with the slides. As mentioned, in some embodiments, manipulation or movement of the slides or the samples may be accommodated. This movement may result in a horizontal or vertical configuration of the slides to facilitate sample processing as described below.

As mentioned above, there may be a large number of process steps accomplished. As may also be appreciated from the nature of the processes envisioned, there may be uses of many different substances or the like. Whether involving a substance or merely a physical action, these types of items may be considered as relating to operationally-influential exteriorly-consequential information. The item may be operationally-influential in that it either its operation or failure in operation may directly or indirectly influence some type of conduct. This conduct may be exteriorly-consequential in that it may be a conduct that does not take place within the process system itself but external to it. As such the present invention may provide the capability to monitor that information. This capability may even be considered as an operationally-influential exteriorly-consequential information monitor 402 as shown generally in FIG. 10. Thus the present invention may include an ability to monitor information of a broad nature.

As but one example, the present invention may involve monitoring exteriorly-consequential information that is actually operationally-altered outside information in that the activity conducted as part of the process system's operation actually causes a change in the information. But one example of this might be using up a particular stain substance. By monitoring this category of information, the present invention may be considered as monitoring operationally-altered outside information. This embodiment may thus be considered as including an operationally-altered outside information monitor. Of course, these events may be influenced at least in part by at least some of the robotic sample process functions.

As previously mentioned, arm 120 may comprise syringe 124. The syringe 124 may be considered a probe in some embodiments, depending upon the requirements of protocols to be performed. Syringe 124 may be fluidically connected with and may apply one or more of the following: rinse agents, such as water; containers, potentially removably fluidically connected for the aspiration of reagents, such as aspiration of reagents from containers and to the samples presented with the carriers; and blow off or other removal agents such as an air source. Syringe 124 may be utilized to pierce processing material containers such as reagent containers. In some embodiments, a reservoir may be provided with the arm 120 to allow for various volumes to be aspirated by syringe 124. The unique configuration of the reservoir allows for efficient cleaning and drying of the internal portions of the syringe while allowing for the accurate pipetting or otherwise aspiration of a wide range of volumes.

Arm 120 may, in some preferred embodiments, comprise a sensor element. The sensor element may be used to automatically determine location and other status information of components of the sample processing system, such as reagent containers, or other processing material containers, or sample carriers. This may be used to teach the system proper and/or actual locations, and to calibrate, self-calibrate, or self-align the system, or the like.

In preferred embodiments, the sample processing system 101 may include an automatic slide identification element. This may be controlled to achieve the act of automatically identifying said plurality of slides. This may also be more generic such as there may be some type of sensor element and it may even comprise a reader or scanner, such as a CCD camera, utilized to determine status information of processing materials, such as reagents as well as to identify slides. The sensor element, for example, may read, detect, or otherwise determine information in the sample processing system 101, for example, from processing material containers, such as, for example, reading coded or perhaps encrypted information provided on the container to determine reagent type and reagent location within the system. The sensor element may also determine status information of sample carriers. For example, in some embodiments, slides configured with a slide retainment assembly may be provided with informational indicia, such as a code, that may indicate information about the sample presented on the slide or the processing protocol to be performed. The sensor element may read the code of the slide to determine the protocol to be performed for the particular slide and sample.

A cleaning station 140, shown in FIG. 1, may be included to clean elements of arm 120, and in preferred embodiments, may function to clean or otherwise remove completely the previously deposited reagent from the probe, or remove elements containing the internal and/or external surface of the probe and/or syringe 124. In one embodiment, the cleaning station may be configured to clean elements of arm 120, such as syringe 124, while such elements are configured with arm 120. The syringe may be cleaned, for example, with a water rinse through the syringe while the syringe is positioned at the cleaning station. In other embodiments of the present invention, the cleaning station 140 may be configured to allow a drop off and pick up of elements such as syringes for cleaning while allowing the processing throughput of the sample processing system to continue.

In some embodiments, multiple probes or syringes may be used to apply fluids required for the staining of histological tissues samples mounted or otherwise presented on slides. This may encompass automatic staining accomplished through a slide stain element such as the items included on the robotic motion system 172 discussed above. The sample processing system may drop off a "dirty", contaminated, or used probe or syringe and swap it for a "clean", uncontaminated, sterilized or an unused one. One or more probes or syringes may be cleaned while the system continues processing of samples, such as applying reagent or stain with an alternate probe or syringe.

The system may access, use and wash multiple probes or syringes for pipetting or otherwise aspirating fluids required for the staining of samples mounted or otherwise presented on slides. To eliminate cross contamination, a system with a single reusable probe may wash the probe between each fluid applied. The task of washing the probe can have a large impact on the throughput of the overall system. The present invention may allow for multiple probes to be available to the system for use. The system may continuously have a clean, uncontaminated, sterilized, or an unused probe available to use and sample processing is not impacted by the required cleaning routine. The cleaning routine may be necessary to eliminate the possible cross contamination of fluids and, in some embodiments, may take up to about 1 minute to accomplish. The cumulative impact of the cleaning routine on a series of processing steps can add time to the throughput capabilities of the system. The addition of multiple probes or syringes may eliminate this impact and significantly decreases the time required to process the samples.

Embodiments of the present invention may comprise a mixing station 150, shown in FIG. 1. The system may mix component fluids, such as dyes, buffers, or other processing materials, preferably on demand and as the processing steps and protocols dictate. Fluids required during the processing steps may sometimes need to be mixed with other fluids to create a final activated fluid mixture or cocktail. However, the activity levels of these mixtures can be time sensitive and may therefore only be effective for a short period of time. The on demand mixing of fluids is advantageous in that it allows the fluids to be mixed immediately before being used. The syringe or probe 124, in preferred embodiments, will aspirate fluids into and from the mixing station 150 to mix component fluids. A rinse may further be dispensed into the mixing station to sterilize the station.

In preferred embodiments, slides are movable and configurable in both vertical and horizontal positions as required for the pretreatment and staining process. This allows for the automation of the pretreatment and staining of slides in various manners, including pretreatment and staining as accepted in conventional manual laboratory methods. The slides are initially loaded into the carrier retention assemblies, such as slide racks, and drawers in the horizontal position. If pretreatment is required, such as deparaffinization, the system rotates the slide into the vertical position and lowers these samples into a processing tank, further described below, filled with the required fluids. In some embodiments, the slide rack is lowered to affect lowering of the slides (see FIG. 2). To perform the staining process on the slides, as described below, the System rotates or moves the slide to the horizontal position and a syringe or probe applies fluid to the sample, providing a horizontal staining of the sample. Each slide can be rotated independently allowing for the independent processing of different samples with different requirements.

The system automates, and in some embodiments mimics or otherwise corresponds to the procedure and physical attributes of the supplies used manually to perform these same pre-treatment processes. Accordingly, a processing tank may be provided. In some embodiments, components of each processing tank may be configured within a drawer 104. In some preferred embodiments, the fluids volume needed to perform pre-treatment processes are maintained but instead of the slide orientation with each other being face-to-face, as in conventional systems, they are side-to-side, although other slide configurations are not disclaimed. The processing tanks provide even distribution of fluids across the face of the slide.

In some embodiments, the processing tanks have the ability to heat and cool the slides. Heat may also be applied to each individual slide by a thermal device. The precision and physical application of the temperature control can result in standardization and repeatability of process steps. Filling and heating tasks are performed by a computer controlled scheduler, as further described below. Fluid volume may be adjusted to account for the presence or absence of any number of slides.

In some embodiments, the individual fluids used for pretreatment may be contained in the system cabinet. Deparaffinization fluids (except DI water) may be drawn into the processing tanks, then returned to their containers for reuse. Containers are as listed for fluids one through six. On a periodic basis, the material in the "dirty" containers may be discarded. The "clean" containers may be moved up to the dirty position, and then fresh fluid added to clean position. DI water may be drawn from the large system DI water container, and discarded after each use. Target retrieval solution may be drawn from dedicated containers, and may be recycled or discarded after each use.

Returning to the aspect of monitoring or capturing information, an embodiment of the system may be designed to monitor replenishable supply information, such as the status of buffers, reagents, stains or the like. By monitoring for a potential need for replenishable supplies the system may not only provide the replenishable supply information monitor 403 shown in FIG. 10, but it may also relieve operators of some concerns. It may also remove at least Ione possibility for human error. Significantly, the system may also act to automatically notify any number of people relative to the information monitored. With respect to replenishable supply information, the system may notify a user, an operator, an administrator, or even a supplier of an actual, potential, or impending need to replenish supplies. As such the system may be considered as including an automatic notice element 404, or an automatic operator replenishable supply notice element, an automatic supplier replenishable supply notice element, or the like.

In a similar fashion, an embodiment of the system may monitor or capture information that is of interest to the continued or continuous operation of the device. As such it may be monitoring instrument maintenance information. This may include, but is not limited to monitoring part cycle information, ranging from a gross information such as age of the device, estimated number of cycles, to even monitoring specific information such as monitoring individual part cycle information (e.g., how many times and actual valve was turned on or off, etc). By including an instrument maintenance monitor, an instrument maintenance information monitor 405, a part cycle monitor, or an individual part cycle monitor 406, the system may facilitate not only enhanced reliability and continuous operation, but it may permit preventative maintenance such as maintenance based on product cycles or mean times between failures. Naturally, it may also use the automatic notice element 404 such as providing an automatic maintenance notice element to inform a wide range of persons of such issues.

Of course, a large variety of information may be monitored; embodiments of the system may monitor or capture information that relates to material requirements, such as expiration dates, lot information or the like. Thus the present invention may include a material requirement information monitor 407 so that it acts to automatically monitor material requirement information. This may be a product expiration information monitor 408 that may even act with respect to an upcoming expiration and may even cause the set of automatically advance notifying a person by providing an automatic advance expiration notice element For items that may be very important there may even be multiple notices either concurrently or sequentially and as such the system may include a multiple advance expiration notice element. Another type of information that may be monitored is historical usage information such as information of a statistical or past nature. Thus the system may include an historical usage information monitor 409. From this, predictive estimates may even be made such as a likely date upon which to order an item or the like. Through monitoring predictive usage information, this may be one way the system may be able to provide an automatic predictive need notice element or even a predictive usage information element 410. It may also provide for a user statistical information monitor so that it can assemble and monitoring user statistical information and act on this such as by comparing to other historical or statistical information or the like. The present invention may also be configured to monitor sample process efficacy information such as by assuring particular protocols are followed or the like and may thus provide a process efficacy information monitor 411. Monitored information may be extrapolated to permit a totalizator 413 capability by adding up individual usages to know amounts left or otherwise impacted by operation. This may include totalizing usage information for an item such as a reagent or an individual part's cycles. Such a capability may serve as a totalization usage information monitor, a reagent totalizator, or a part cycle totalizator. By having a data capture element 414, the system may generate data that may include or permit analysis or use of a variety of aspects, including but not limited to: number of occurrence data, part operation data, amount of usage data, and amount of material used data. Such data may, of course, have a like element, perhaps a subroutine, to do or generate the various function or data involved.

In some embodiments, an imaging device such as an image-capture 2-D optical sensor, perhaps a CCD camera, or the like, may be used to determine the position of the sample on the slide, providing for greater accuracy during sample processing. Embodiments of the sample processing system 101 may further provide sample diagnostic capabilities. Accordingly, in some embodiments, a device may analyze samples. A camera may be used for diagnostic purposes. In some embodiments, the sample may be scanned for further analysis, potentially by computer. The camera can also be used 1) as an area locator, 2) to locate a tissue area, 3) to, apply reagent based on location and area. The scanned image may be analyzed for reagent analysis or other analyses.

The system may also generate or also monitor subject sample data. Relative to the, imaging device, the system may monitor or perhaps capture image data, such a sample image data, substance image data, system image data, and even pre- and post-event image data. Each of these may be systematically stored for some purpose. Each of these may correspondingly be considered to present an appropriate element such as a system image data capture element, a substance image data capture element, a sample image data capture element, and a pre- and post-event image data capture element. In addition, there may be included a multiple image data capture element so that more than one image may exist to prove or evidence an aspect of the processing. Again, the system may act to systematically store and one or the multiple images so created. Collections of like data, such as groupings of individual sample process data, individual slide log data, and even type of protocol data may also be created.

Figure 4:
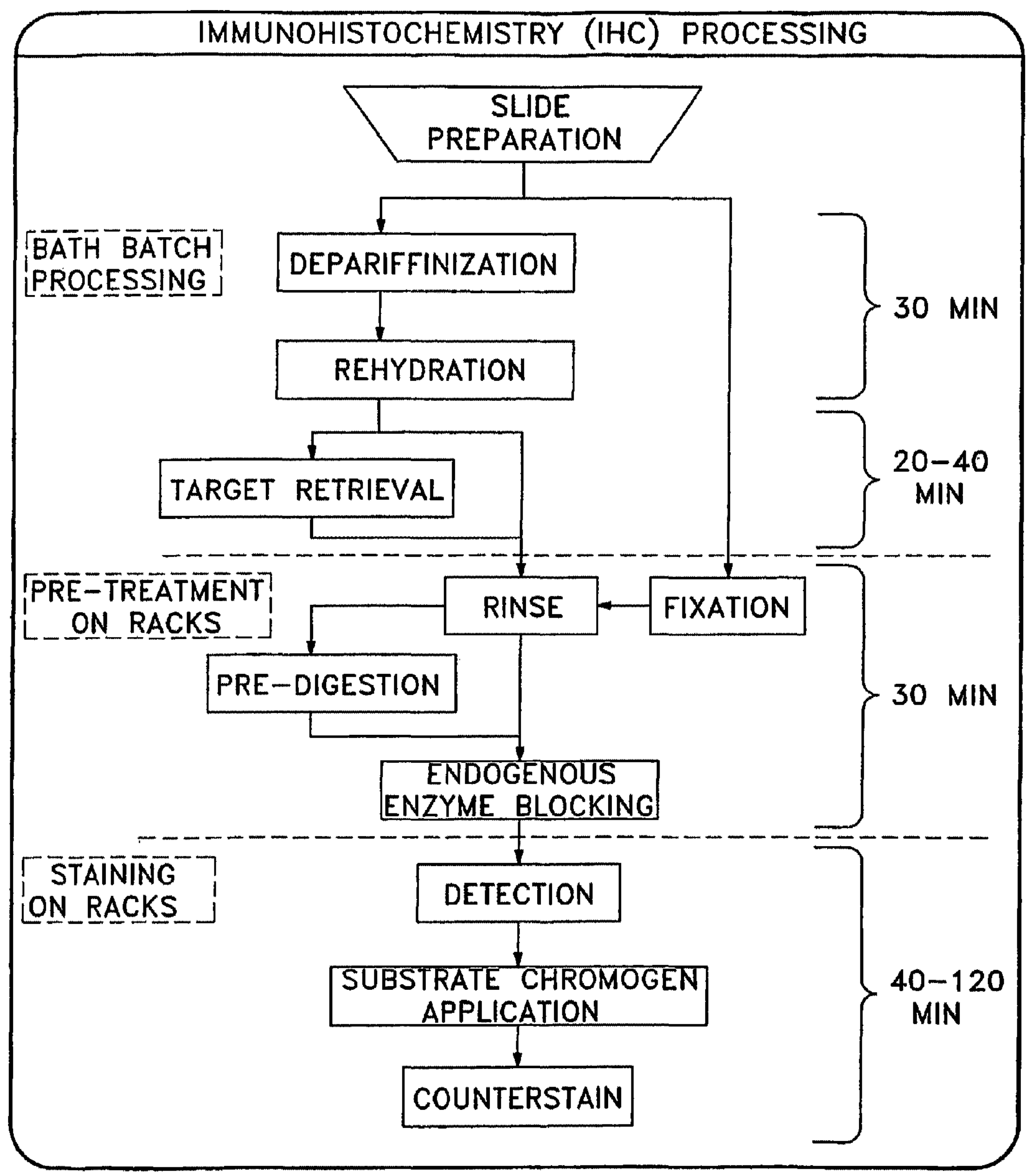
FIG. 4 is a flow chart of some representative process steps of an embodiment of the invention.

The processing of samples may be accomplished according to some preferred embodiments as shown in FIG. 4 and FIG. 11 consistent with features of the present invention. Variants of these protocols and processing steps, or other processing steps, may be accomplished consistent with the present invention.

One processing sequence may broadly comprise the preprocessing of a sample, if needed, such as deparaffinization (as previously described), and further comprise target or epitope retrieval (as previously described), and sample staining.

In some embodiments, specifics of in-situ hybridization (ISH) may be addressed. Embodiments of ISH may require a small volume of reagent, such as 15 microliters, to be placed on the sample. Heat control may be maintained between about 95-100 C and kept constant for a period of time. Temperature may then be lowered in a controlled manner.

Furthermore, fluorescent staining or tagging in IHC or ISH (FISH) may be performed consistent with the features of the present invention.

As mentioned, the sample processing system may automate the processing of samples mounted on carriers or slides. This configuration of the system allows for the flexibility for both continuous, individual, and batch processing of slides with the design lending itself to meet established laboratory workflow demands. The multiple independent and redundant slide processing subsystems found within the system may also maintain its ability to process each slide independently.

The automatic processing may be achieved by designing a system with automated process operation capability or sequencing through at least some steps without human intervention that may be controlled by or act in response to a process operation control system 171. This may be provided through hardware, software, or some combination of the two. One conceptual embodiment depicts some of the various capabilities in FIG. 10. Of course, the user needs the ability to specify the nature and sequence of the various steps or acts desired. This can be accomplished by an input parameter capability 173 through the inclusion of even a sample process parameter input 173. This input can be retained by the creation of stored parameter process data 174. In order to facilitate uninterrupted processing, the input parameter capability 173 may be configured as an independent process parameter input with respect to the process operation control system 171, such that acts caused by the process operation control system 171 are unaffected by any action with respect to the independent process parameter input. Further, the input parameter capability 173 may also be configured as an autonomous input functionality through the inclusion of an autonomous input element.

Capabilities may not only act independent of the automated process operation capabilities, but they may be fully functional even without the presence or operability of the automated process operation capability (which itself may or may not be in a process device). This may be achieved in a variety of manners, including by providing a separate full function computer 181 (e.g., separate from the capability provided or required by a process system) or that may be programmed to accomplish the input. In addition, in order to accomplish a goal of addressing practical and institutional needs, any capability may be configured to provide simplified use and may even be available in a highly simplified level of detail. This may be a "wizard" type of system where there is a "step-by-step" method for functions such as programming slides, adding slides, achieving the desired input, or the like. Such an aspect may even be simple, regimented, and somewhat inflexible. A structured or simplified input can facilitate input by persons not required to have the full spectrum of skills necessary to be responsible for the operation of the sample processing system 101.

As part of the functions of monitoring or perhaps allowing play back of events, the system may include some type of data capture element 414. As may be appreciated from the initial discussion of the types of actions potentially needing to be programmed, the data capture element 414 may capture individual movement data, only robotic action data, individual robotic movement data, individual operation data, or even individual usage data. Thus the data capture element 414 may be an individual movement data capture element, a robotic action data capture element, an individual robotic movement data capture element, or an individual operation data capture element. All or any part of this data may be systematically stored such as storing all important details, only particularly important details (e.g., relative to highly sensitive valves, substances, or the like) or even only a significant number of details relative to sample process operations. Thus the data capture element 414 may be a systematic process detail capture element. Once captured, this data may be stored in a number of fashions. There may be a memory location at which such data resides and this may thus represent a significant process detail memory 412. It may also represent a subject sample data capture element and any of the memory types mentioned earlier may be used for such a purpose.

In storing the data, the system may create a segmented computer file, that is a file that contains only such data so that it is not as manipulatable as other files. This may aid in assuring the accuracy or even certifiability of the events depicted. For instance for any particular sample, there may be automatically generated upon request a simulation—perhaps with a time base appended—of what happened to that particular sample as well as pictures of the sample before and after its processing. The data so stored may even be created as an inalterable computer record and perhaps may even include an integral change indicia that can prove its accuracy. When stored, the system may create a common format computer record so that user can easily work with it or it may create a proprietary format computer record that cannot be altered or the like. Thus the significant process detail memory 412 may represent a segmented computer file memory element, an inalterable computer record memory element, an integral change indicia memory element, a common format computer record memory element, or a proprietary format computer record memory element.

The capture of data may include time of occurrence data, such as actual date data, actual time data (e.g., UTC, etc.), precise time data (e.g., hours, minutes, seconds), relative time data, absolute time data, initiation time data, and even completion time data (e.g., process, protocol, motor operation events, or the like). Again, the data capture element 414 may include, but is not limited to, a time of occurrence data capture element, an actual date data capture element, an actual time data capture element, a precise time data capture element, a relative time data capture element, an absolute time data capture element, an initiation time data capture element, or a completion time data capture element.

One item that may be of particular user desire is the fact that the data capture element 414 may represent an individual sample process data capture element, an individual slide log data capture element, a type of protocol data capture element, and even an individual slide log data capture element. There may also be a real time individual slide log data display to show actual processing as it occurs.

Figure 8:
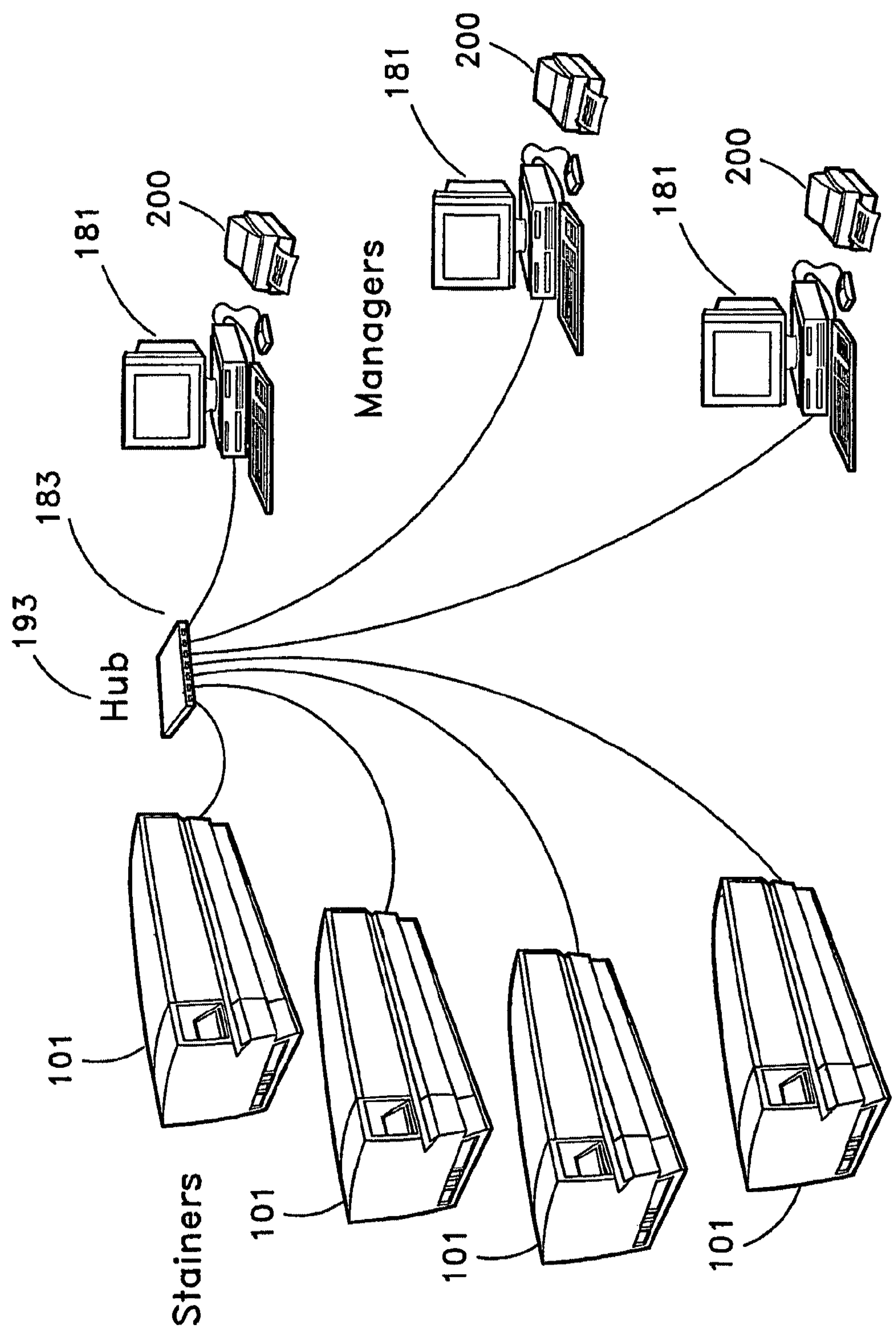
FIG. 8 is a depiction of an embodiment connecting multiple stainers with multiple managers and multiple label printers.
Figure 9:
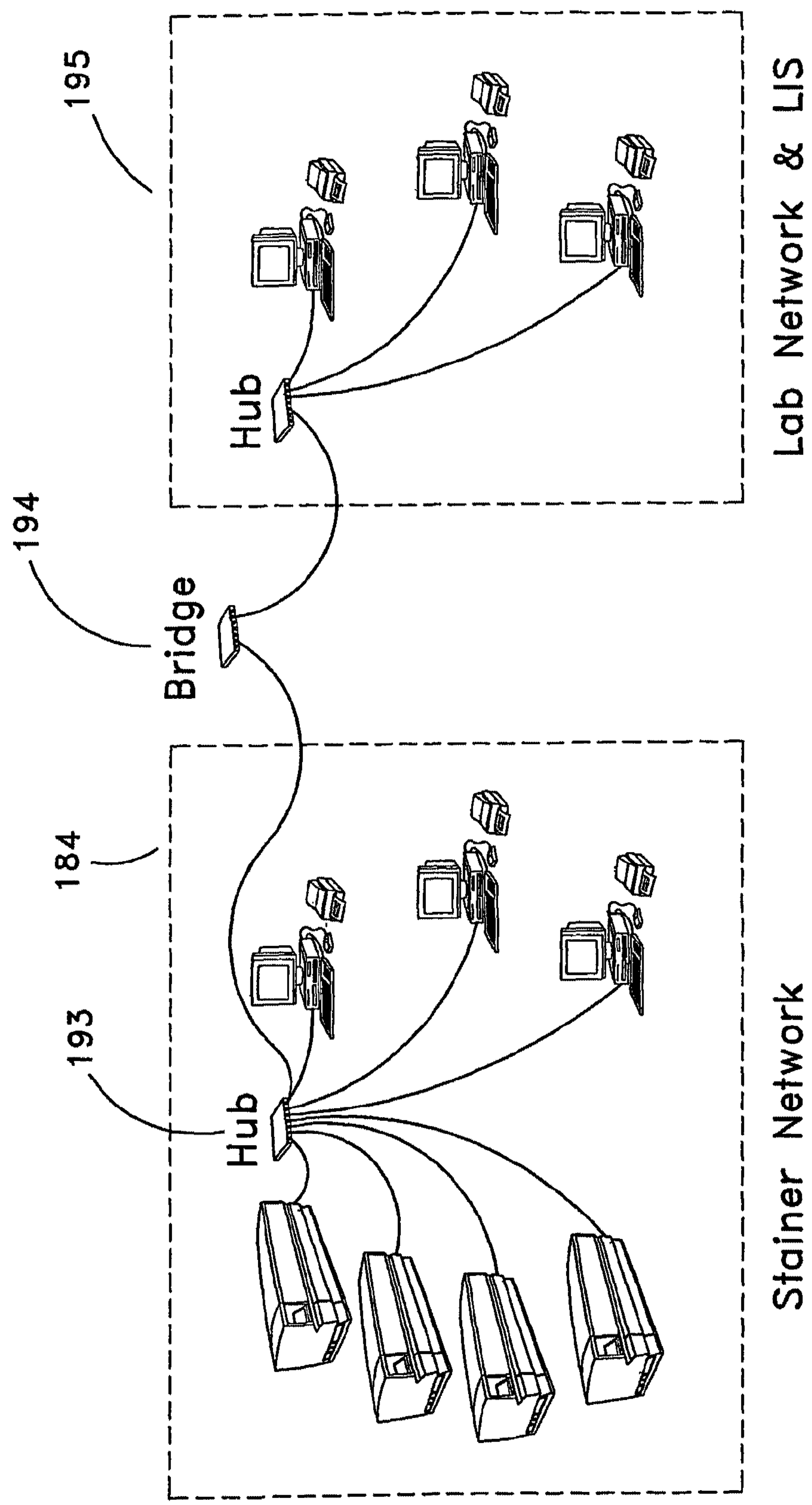
FIG. 9 is a depiction of an embodiment connecting a system to a lab network and lab information system.

As used above, the slide identification information may represent any information unique to a particular slide, such as a serial number, patient number, patient name, unique image, or the like. In keeping with privacy concerns, there may also be coded or perhaps encrypted identification information or internal identification information that others cannot use to identify the particular patient involved or the like. As discussed below and as shown in FIGS. 8 & 9, the overall system may include a number of staining instruments and thus the input can include preferred stainer information (which may or may not be indicated or accepted by the automated system). Provision can also be included to achieve a rush test and as such there may be an immediate, urgent, or otherwise known as stat (an often used medical term for immediate) process request information element. Such may also be linked with user privileges information so that only certain individuals may displace other tests to create a different priority. Of course all permutations and combinations of the above may be included.

For automated operation, the input may create data such as parameter process data 174 that may be stored at some location. To provide autonomous operation, it may be independently stored perhaps in a physically independent memory even at a location remote from an actual stainer itself This may be accomplished by utilizing a primary or secondary storage perhaps of a separate full function computer programmed or configured to accept and/or store data. In such a fashion, the computer may contain what could be considered as an independent process parameter memory 174. Since the computer is likely physically separate, it may be considered to have a physically independent memory perhaps even a remote location memory if it is remote from the process equipment.

By using independent memory and independent other functionality, the system may facilitate full operational functionality of the automated process operation capability. Since the automated-process operation capability is fully operational during operation of either the memory or input, the storing or inputting or other function can be conducted without interrupting the process operation. Thus the inputs can be later accessed at a process time independent of the time of accomplishing slide process parameter input or storing. In addition, entry or storing may also be accomplished at least in part concurrently with the processing of certain samples. This processing may even be initiated significantly after completion of the slide process parameter input action. Such may occur at least about one hour after the input, at least about three hours after the input, at least about eight hours after the input, at least about one day after the input, at least about two days after the input, and at least about one week after the input.

As mentioned briefly above, once the information is either monitored or captured, the present invention may act to automatically inform at least one person who may find the information useful. The automatic notice element 404 mentioned earlier may be configured to act as an automatic exteriorly-consequential information notice element by relating largely to that type of information. Of course, the automatic notice element 404 may act in response to the step of monitoring the particular information involved. For example, if it is monitoring operationally-altered outside information, the automatic notice element 404 may act as an automatic operationally-altered outside information notice element. For process events that are merely captured and not automatically monitored, a person may prompt the system upon which it may provide information by some type of display 415. This display (in its broadest sense) may reveal at least some information, perhaps relative to sample process operations to at least one person. If the display reveals significant process detail information, it may be considered as a significant process detail information display. Further if it displays at a separate location there may even be a significant process data transfer element to facilitate remotely displaying such information. As such the display 415 may be considered a remote process detail information display. As mentioned earlier, the system may provide for a real time information display, that is a display that reveals information at about the time it occurs. By real time displaying information remotely, the operator or any other interested person may be able to "watch" or monitor the progress of the instrument from another location—perhaps even the other side of the world. This may be particularly valuable when there is a real time display of individual slide log data as mentioned above.

One type of display 415 that may be noteworthy is the fact that embodiments of the invention may create a simulated motion display. The simulation may visually show an element moving on a screen just as the robot head actually moved when it operated. Embodiments can provide sequential playback capability so that one could also "watch" the instrument just at it operated at some earlier time. There may also be an altered speed sequential playback capability, a user alterable speed sequential playback capability, or merely a high speed sequential playback capability perhaps all with or without pause or slow motion capability. With this capability, the display 415 may represent a simulated motion process detail information display. The system may thus include a sequential playback element, an altered speed sequential playback element, a user alterable speed sequential playback element, and a high speed sequential playback element.

All this information must, of course be used by some person. Any interested person may have the information available to them, such as an operator (e.g., anyone responsible for all or a portion of a process or the instrument), an instrument operator (e.g., an individual physically responsible for all or a portion of a process), an administrator (e.g., a person managing operators or perhaps responsible for order placement), a substance or other supplier, or even a manufacturer, such as for support and maintenance capability. For events that may require external actions (e.g., ordering more reagent or the like), the system may automatically notify at least one of these types of people and thus the automatic notice element 404 may be considered as representing an automatic operator notice element, an automatic administrator notice element, an automatic supplier notice element, or an automatic manufacturer notice element. It may also be considered as representing an automatic operator exteriorly-consequential information notice element, an automatic administrator exteriorly-consequential information notice element, an automatic supplier exteriorly-consequential information notice element, or an automatic manufacturer exteriorly-consequential information notice element.

Notice may be given at a variety of times. The system may act to automatically advance notify a person such as of an upcoming expiration date or of a need to reorder in advance. In so doing it may have or have input to it some type of lead time information that tells it how early to take the action. By properly configuring a lead time information data element 416, lead time may vary by location and situation, for example a machine. around the world or used continuously for critical processing may have a longer lead time than a machine right next to a supplier or used only sporadically. Order lead time information, reagent orderlead time information, maintenance lead time information (any of which may vary over the course of a year or from time to time) may be utilized and as such the lead time information data element 416 may represent an order lead time information data element, a reagent order lead time information data element, or a maintenance lead time information data element.

Notice itself may be displayed in a variety of ways. The system may automatically E-mail a person through inclusion of an E-mail notice element; it may automatically print out (including faxing) a notice by having an automatic printout notice element. Among other possibilities, it may automatically utilize a telephone line for simulated or reproduced voice or other information by having an automatic telephone line utilization element.

Figure 6:
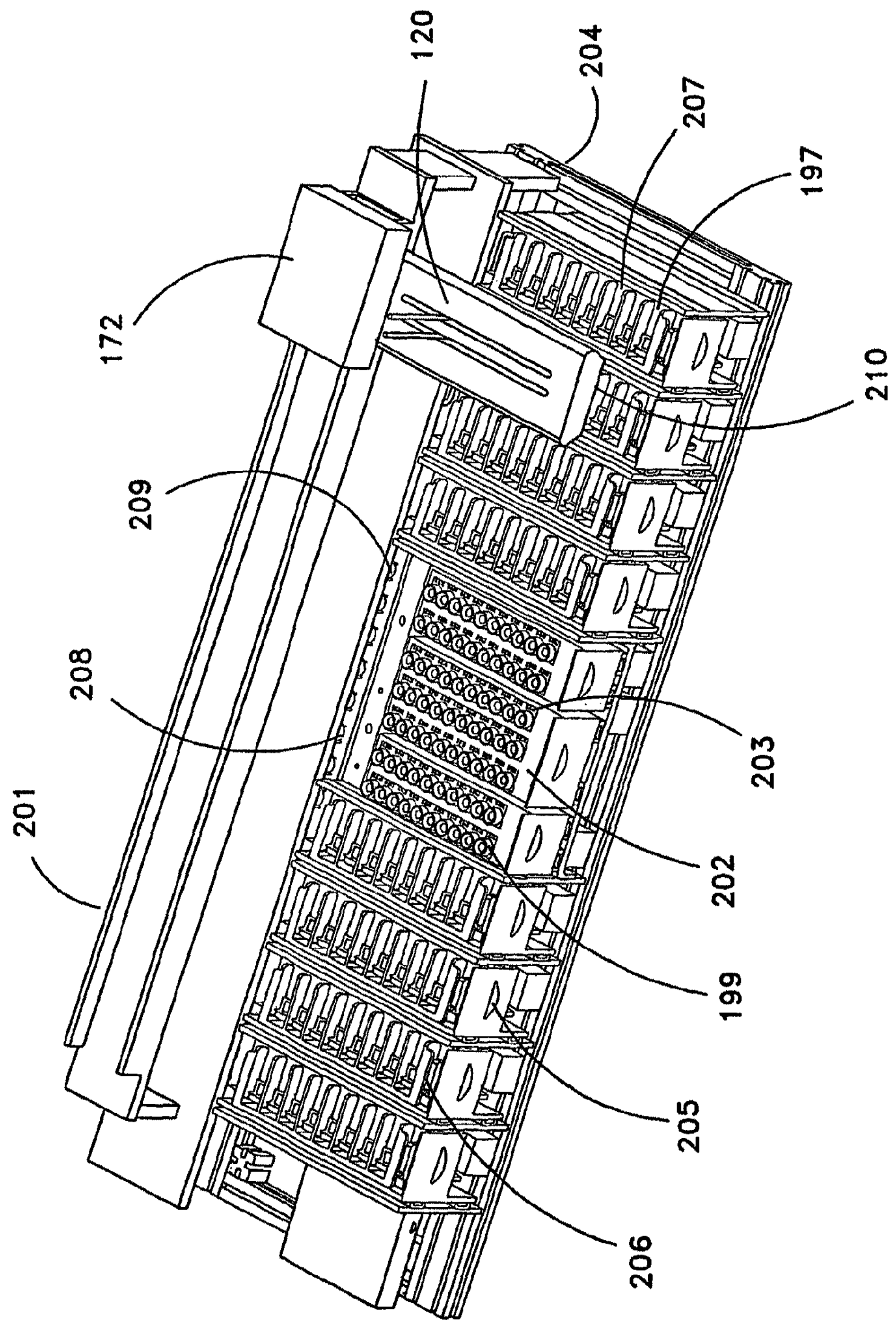
FIG. 6 is a depiction of an embodiment of a device incorporating some of the features of the invention.
Figure 7:
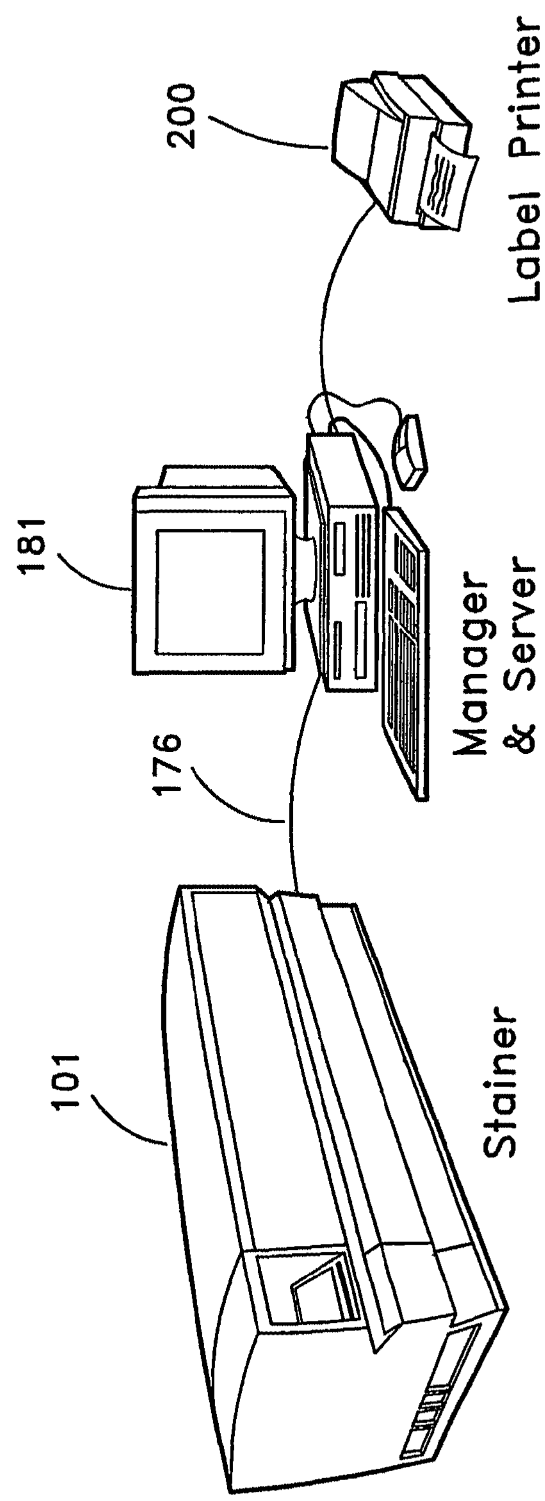
FIG. 7 is a depiction of an embodiment connecting one stainer with one manager & server and one label printer.

The actual event of providing notice may be automatic or it may by caused by some type of user prompt 417. By accepting a monitored information user prompt the system may represent a monitored information user prompt. The prompt itself may be a mere software selection or even a mere click-on items such as a software displayed button or the like. Whether displayed and acted upon remotely or at the actual robot-containing housing, such a user prompt 417 may cause a remote access connection to be established and as a result at least some significant process data may be displayed. In such a manner the user prompt may represent an information access prompt element, a software selection element, or a remote access element In some embodiments, the system may be comprised of independent or perhaps redundant slide staining modules (some embodiments may comprise eight modules) as shown for some embodiments in FIGS. 1 and 6. Throughput may be based on the time to first result with the system allowing access to completed slides as soon as a staining module has completed the scheduled staining tasks. The multiple independent or redundant staining modules may allow for both continuous and batch processing of slides. Additionally, each independent staining module may also allow for the independent pre-treatment and staining of each slide. A carrier retainment assembly, such as a slide retainment assembly, may be used to introduce slides to be processed into the drawer 104, the drawer, slide retainment assembly, and components thereof forming a stain module. The slides may occupy one or more positions of the slide retainment assembly, such as at carrier retention devices, up to the capacity of the slide retainment assembly with the potential for each slide being processed independently of other slides configured with the slide rack. Embodiments of the stain modules, drawers, slide racks, and components thereof are also shown in FIG. 6. FIG. 6 also provides other embodiments of system features, such as an embodiment of the arm 120 and the component features of the arm.

Slide retainment assemblies having one or more slides and even reagent containers may be introduced into the staining or reagent modules by introduction into drawers 104 one at a time or in any combination until all or an appropriate number of staining modules are appropriately occupied. There may be no restrictions as to the order, number or timing of when the slide retainment assemblies are introduced into the system, the system may also allow for adaptive scheduling of sample loading. Staining modules, and in some embodiments the drawers of the staining modules, may lock out access to the slides during the processing period and may release them to the operator upon completion of the staining or other process on the last slide of that module. In some embodiments, the order in which the slide retainment assemblies are released may be dependant on the time required to process the last slide of the retainment, assembly. Slides may even be processed in the most time efficient manner independently of the order to which they were introduced into the system. The system may provide an optimum or merely an enhanced temporal scheduling of the various sample process steps. To accomplish this, the system may automatically schedule steps that are interspersed for an enhanced time result This interspersing may be an interleaving of a number of process operations and even an interleaving of a number of individual sample operations. In addition to interleaving steps, the system may sequence the individual sample operations. Regardless as to how programmed, it may be configured through hardware or software or a combination of each to provide an enhanced temporal scheduler element 179, a process operations interleave element, an individual sample operations interleave element, or even an individual sample operations sequence element. These can be created by integrating the automated process operation capability and either the parameter data or perhaps some replicated portion of that parameter process data (as mentioned later) and can thus act to create an interspersial robotic control functionality 175.

The control of the processing samples may be accomplished according to the following preferred embodiments, one preferred embodiment shown in FIG. 5, although other processing may be accomplished consistent with the present invention.

As shown in FIGS. 8 & 9, in expanded systems, a sample processing system manager, such as a computer server may be connected with a number of individual sample processing systems. These may represent automated slide stainers or even stand alone automated slide processing system such that they are fully capable of functioning with connection to other devices. In systems where a connection does exist, the capability of electronically connecting a number of automated slide stainers or automated sample processing systems or label printers 200, may be provided. As mentioned earlier, there may be one or more separate full function computers connected. These may be connected through a hub 193. There may be a multitasked central processing unit resource on either the stainer or the computer or there may be a number of of central processing units that are configured to avoid using or implementing a multitasked central processing unit resource relative to the process operations in order to maintain full independence or perhaps even autonomous operation. The connection, whether for input or other operation may also be a remote link (including ability to be made remote such as in detachable memory) such as an internet connection element, a telephone line connection element, a wireless communication element, or even a detachable memory element. In a preferred embodiment, connection among perhaps a number of process systems and perhaps a number of computers, such as workstations and a server (the latter residing either separately or as part of a workstation), may be achieved by use of a local area network (LAN), such as a group of computers and associated devices that share a common communications line or perhaps wireless link and may even share the resources of a single processor, memory, or server within a small geographic area (for example, within an office building or complex). A local area network for this type of system may also include features such as but not limited to: an Ethernet element, a token ring element, an arcnet element, a fiber distributed data interface element, an industry specification protocol, a bluetooth-based element (named but not contemporary to King Harald Bluetooth of Denmark in the mid-tenth century!), a telecommunications industry specification using a frequency band of 2.45 GHz, a communication specification applying an IEEE 802 standard, a frequency hop communication specification, a shared common link element, a transmission control protocol/internet protocol communication element, a packetized information protocol, a shared protocol, a proprietary protocol, and even a layered protocol exchange system. By providing an electronic connection 176 between various resources, the local area network such as the stainer network 183 (a network dedicated to only the stainer or perhaps sample processing resources for integrity, security, and other purposes) in one embodiment may transmit a electronic memory address to achieve access to the appropriate information. Connection may also be established to a lab network, facilities intranet system, or even a lab information system 195 such as through a bridge 194.

As mentioned, connection may be accomplished over internet connections but more preferably is accomplished over local area network connections. Each sample processing system may be individually controlled, in some embodiments, by a PC attached with, internal to, or otherwise provided. Data sharing between sample processing systems and the system manager may be performed to allow identification, tracking, and status of sample batches, reagents, and other agents and components of the sample processing system. A determination of which system has which reagents, reagent type, slides and protocols may be performed. Log files for each processing sequence, protocol, or slide can be generated for monitoring processing status. Database maintenance (including but not limited to purge, compact, backup, database/list functions) and system diagnostics (including but not limited to exercising active system components to verify proper operation and assisting in troubleshooting efforts) may be accomplished manually or automatically.

The system may be configured to automatically access the required data through operation of the process operation control system 171 by inclusion of an automatic memory access element This access may be achieved by specifying an electronic memory address that may be transmitted by a electronic memory address element 178 perhaps over a local area network and may be followed by automatically replicating that data on some a memory aspect appropriate for operation such as an automatic data replication memory. This memory may include but not be limited to: a volatile memory functionality as implemented by a volatile memory element, a random access memory functionality as implemented by a random access memory element, a non-volatile memory functionality as implemented by a a non-volatile memory element, an electrically erasable programmable read only memory functionality as implemented by an electrically erasable programmable read only memory element, a main storage functionality as implemented by a main storage element, a secondary storage functionality as implemented by a secondary storage element, a cache memory functionality as implemented by a cache memory element, and even a detachable memory functionality as implemented by a detachable memory element.

A control interface may be provided for the operator, such as a graphical user interface (GUI), and may accommodate various languages. Help menus may be provided to assist in sample processing. Password protection features can be provided and even administrator control over at least some aspects. This may include the capability to include administrator limitations on the functional availability of any aspect of the system or of specific stainer availability or functionality, certain reagent availability functionality, certain protocol availability functionality, patient identification information access functionality, process priority request functionality, and immediate, urgent, or stat process request functionality. By including an administrator control element 180, the system may have an administrator-implemented user limitation element, a specific stainer availability limitation element, a certain reagent availability limitation element, a certain protocol availability limitation element, a patient identification information access limitation element, a process priority request limitation element, an immediate, urgent, or perhaps stat process request limitation element, a user privileges input element, and even a user group privileges configuration or input element.

Control of the sample processing may be accomplished by a dynamic scheduling algorithm, and in some embodiments, in accordance with continuous, or batch processing previously described. The processing sequence may be controlled, in preferred embodiments, such that the various steps of a protocol for samples may be automated by one or more algorithmic controls. As part of input to establish the desired control functionality, user or other input may be accommodated as follows: 1) selecting a first protocol step, 2) selecting a second protocol from a restricted list of menu items that are compatible with the first protocol step, and 3) selecting subsequent protocol steps from a restricted list of menu items that are compatible with the preceding protocol step.

After all data is input, the system may act to determine operational readiness by inclusion of an operational readiness determination element 177 that may be programmed to assess if appropriate resources, drawers, slides, reagents, or other aspects are present or available to the system. Once an appropriate operational readiness is determined, the system may prompt initiation of access of the input data to electronically determine operational availability of a variety of items. These may include but are not limited to: an individual sample element through inclusion of an individual sample readiness determination element, a defined group of samples through inclusion of a defined group of samples readiness determination element, a physically grouped collection of samples through inclusion of a physically grouped collection of samples readiness determination element, a slide drawer component through inclusion of a slide drawer component readiness determination element, a stand alone automated slide processing system through inclusion of an stand alone automated slide processing system readiness determination element, a slide stainer system element through inclusion of a slide, stainer system readiness determination element, and even a user initiated prompt signal such as might occur to force or activate the system manually by the inclusion of a user initiated prompt signal determination element.

There may even be timing tolerances, referred to in some embodiments as "bubble tolerance", that may be controlled as between steps, such as between aspiration cycles. Additional control may be accomplished through timing algorithms to determine time tolerances of components of the processing system, such as the monitoring of "shelf life" or viability of reagents. Furthermore, adaptive scheduling of sample and slide insertion and removal into the system, as previously described, may be accommodated on an on-going basis throughout operation of the sample processing system.

One aspect of the invention focuses on an automated staining apparatus and a method of automated treating of samples. As to this aspect, the present invention relates to an automated staining apparatus for treating samples arranged on carrier elements or means, such as but not limited to microscope slides, located at defined positions close to or in the apparatus by removing a portion of selected reagent from a station containing a plurality of reagents and thereafter applying the reagent to a sample, e.g. a tissue, organic cells, bacteria etc., arranged on the carrier means. This aspect of the invention facilitates that two or more reagents are mixed and the mixture applied to a sample. It also relates to a method of automated treating of samples by mixing reagents and applying the mixture to the samples.

Staining apparatuses for staining and treating samples by means of a probe normally comprises a first station for. containing one or more reagent vials; a second station for mounting slides, a probe arranged for removing a portion of reagent from a selected reagent vial and applying the reagent to a slide on which the sample is arranged and a drive means for moving the probe between the various stations.

An object of this aspect of the present invention is to improve the known apparatuses for staining samples as well as the method for automatic staining of samples by facilitating a wider range of available processes or procedures used to implement treatment, so as to ease the implementation of different staining and/or treatment processes that may be performed automatically, alternatively or additionally to provide an increased quality of some specific staining processes.

The term staining is used for the end product of the process, by which certain parts of the sample may be stained, i.e. has obtained a different colour, either in the optic range or in another electromagnetic range, such as ultra violet, or the staining may be an detectable, preferably automatically detectable, change in properties, such as fluorescent properties, magnetic properties, electrical properties or radioactive properties. To obtain the staining, the sample normally has to undergo a series of treatment steps, such as washing, binding of reagents to the specific parts of the sample, activation of the reagents, etc. and each treatment step may include a plurality of individual treatments.

In some staining processes, it may be required for one or more treatments to use a mixture of reagents prepared from two or more separate reagents which may be somewhat incompatible e.g. unmixable, such as a water based and an oil based reagent, or insoluble, and therefore requires that the two or more reagents are manually prepared and introduced into a reagent vial shortly before starting the staining process in order to obtain the best possible staining result for the selected examination purposes. For other processes, different staining process steps require a mixture of the same two reagents but in different dissolved ratios. Some process steps require mixtures of two or more reagents that, when mixed, have a limited time window of usability because internal chemical processes deteriorate the mixture. By providing a staining apparatus having an automated mixer integrated therein, these types of staining processes can be performed automatically instead of requiring human interaction or manual performance of some process steps in a much more automated process, and the quality of the staining process may be improved as a desired degree of mixing of reagents may be provided or an optimal application time window for a deteriorating mixture may be reached.

The carrier elements or perhaps means are preferably arranged in groups or series on trays or the like, so that a plurality of carrier means may be removed from or situated in the apparatus simultaneously, and the apparatus preferably also comprises means for performing the intermediate storage of the carrier means with samples thereon and the removal of the carrier means from the apparatus automatically.

The operation of the staining apparatus may generally be controlled by means of a control element or perhaps a control means, typically a computer having a central processing unit and one or more memory units associated therewith, an control element or perhaps a means for controlling the various operations of the apparatus by controlling stepper motors, solenoids, valves and/or other drive or control parts of the apparatus. The control means may have one or more data communication ports for enabling data communication with external computers by wire or wireless. The control means does not have to be physically arranged within the apparatus itself but may be a computer external to the staining apparatus and connected to the apparatus via a data transmission port thereof.

The operation of the staining apparatus will generally be controlled by means of control means, typically a computer having a central processing unit and one or more memory unit associated therewith, means for controlling the various operations of the apparatus by controlling stepper motors, solenoids, valves and/or other drive or control parts of the apparatus. The control means may have one or more data communication ports for enabling data communication with external computers by wire or wireless elements. The control element or perhaps means does not have to be physically arranged within the apparatus itself but may be a computer external to the staining apparatus and connected to the apparatus via a data transmission port thereof.

The present invention also relates to a method of fully automated treating of samples arranged on carrier elements by means of a staining apparatus controlled by means of a control element or means, wherein the method comprises the steps of situating a plurality of carrier means intermediately in a carrier means station, each carrier means having a sample arranged thereon, applying a portion of a first reagent selected from a plurality of reagents to a mixing cup, applying a portion of a second reagent selected from a plurality of reagents to the mixing cup, mixing the reagents in the mixing cup by means of mixing means, moving a probe to the mixing cup by means of a probe drive means, removing a portion of the mixed reagents from the mixing cup by means of the probe, moving the probe to a selected one of said carrier means, and applying the mixed reagents to the selected carrier means, so as to perform a treatment of the sample arranged on the selected carrier means.

The present invention further relates to the use of an apparatus of the present invention as described above for exercising the method of the present invention.

The embodiment shown in the figures and described in details below is only an example of an apparatus in accordance with the present invention and is not limiting the wider scope of the invention as described in the enclosed claims.

As shown in FIG. 6, a detailed description of one embodiment of this aspect of the invention involves staining apparatus 201. The staining apparatus 201 may comprise a rectangular frame 204 surrounding a first station 202 comprising an array of compartments wherein each compartment a reagent vial 203 is placed, and a second station 205 wherein a number of separate racks 206 is placed, and where each rack may comprise a number of slides 207 mounted side by side in the rack 206. In the embodiment shown, each rack may hold up to 17 slides, but the rack may be designed to hold any suitable number of slides. With eight racks arranged side by side, the shown embodiments may hold up to 136 slides 207 each having a sample, e.g. a tissue mounted on the upper side of the slide, so that reagent may be applied from above to the sample on each slide.

A robot arm to move a probe 210 in X and Y direction as indicated by the arrows X and Y may be arranged above the frame 204 of the staining apparatus. The robot arm may therefore position the probe 210 above all reagent containers 203 as well as above all the slides 207, and may further operate the probe 210 to remove portions of a reagent contained in any of the containers 203, to transfer the portion of reagent and apply it to any of the slides 207 in order to provide a selected staining or treatment of the sample on each slide 207. By use of a suitable control element, e.g. a computer having the appropriate software, subroutines, or input data for the purpose, this staining apparatus 201 may be able to automatically stain or treat samples requiring different staining or treatment reagents and processes.

Having the appropriate input data, the control element or perhaps means of the apparatus may operate the robot arm to commence a staining or treatment run by moving the probe to a first reagent container 203, into which the probe tip is inserted and liquid is aspirated up into the probe 210 in an amount corresponding to the number of samples to be stained or treated, in accordance with the input data provided to the control element. Additionally, under certain conditions, the instrument may be required to perform a reagent inventory before a staining or treatment run can commence. This inventory may be accomplished by use of the probe tip to actually touch the liquid surface in each reagent vial 203. To prevent cross-contamination between the reagents in the various containers 203, a cleaning of the probe 210 or at least the probe tip may be required after each measurement of a reagent level.

The probe 210 may be moved by the robot arm towards the slide retainment assembly 205 in which the slides 207 are mounted. The slides 207 may be situated with the surface horizontally oriented and the probe 124 may dispense the required amount of reagent on the appropriate slides in accordance with the input data. Alternatively, the probe 124 may be moved by the robot arm towards the reagent mixer 209 where it may release reagent into the cup of the reagent mixer 209, and may be subsequently moved to the probe washing station 208. The robot arm may move the new clean probe to a second selected reagent vial 203 for collecting a selected amount of reagent from the second vial 203, and the probe may thereafter by means of the robot arm be moved to the reagent mixer 209, where the reagent in the probe 210 may be released into the cup of the mixer containing the first selected reagent. This may be commenced several times if more than two reagents are to be mixed for a specific staining or treatment process.

An object of the present invention is to provide a staining apparatus and a method for automatic staining of samples, in which the total process time for completing or even entering the staining protocol may be reduced. In particular, it is an object of this aspect of the invention to reduce the amount of time needed in general.

As can be easily understood from the foregoing, the basic concepts of the present invention may be embodied in a variety of ways. It involves both sample processing techniques as well as various systems, assemblies, and devices to accomplish sample processing, input, and other functions. In this application, the sample processing techniques are also disclosed as part of the results shown to be achieved by the various systems, assemblies, and devices described and as steps which are inherent to utilization. They should be understood to be the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Importantly, neither the description nor the terminology is intended to limit the scope of the claims which may be included at any time.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon at any time.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "retention element" should be understood to encompass disclosure of the act of "retaining"—whether explicitly discussed or not—and, conversely, were there effectively disclosure of the act of "retaining", such a disclosure should be understood to encompass disclosure of a "retention element" and even a "means for retaining". It should also be understood that in jurisdictions where specific language may be construed as limiting, as but one example in the United States where some interpretations of "means for" elements can be construed narrowly, broader equivalent language may be used and should be understood as encompassed by this specification. Such changes and alternative terms are to be understood to be explicitly included in the description.

Any patents, patent applications, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference as well as the definitions presented by searchStorage.com, such to be considered as representing the meaning of the terms as understood by computer professionals. Finally, any priority case for this application is hereby appended and hereby incorporated by reference.

Thus, the applicant(s) should be understood to have support to claim at least: i) each of the sample processing systems and subsystems as herein disclosed and described, ii) the related methods disclosed and described, iii) similar, equivalent, and even implicit variations of each of these systems, assemblies, devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and systems, assemblies, devices, and apparatuses substantially as described hereinbefore and with reference to any of the accompanying examples, x) the various combinations and permutations of each of the elements disclosed, xi) each potentially dependent claim or concept as a dependency on each and every one of the independent claims or concepts presented, xii) processes performed with the aid of or on a computer as described throughout the above discussion, xiii) a programmable system as described throughout the above discussion, xiv) a computer readable memory encoded with data to direct a computer comprising means or elements which function as described throughout the above discussion, xv) a computer configured as herein disclosed and described, xvi) individual or combined subroutines and programs as herein disclosed and described, xvii) the related methods disclosed and described, xviii) similar, equivalent, and even implicit variations of each of these systems and methods, xix) those alternative designs which accomplish each of the functions shown as are disclosed and described, xx) those alternative designs and methods which accomplish each of the functions shown as are implicit to accomplish that which is disclosed and described, xxi) each feature, component, and step shown as separate and independent inventions, and xxii) the various combinations and permutations of each of the above.

Further, if or when used, the use of the transitional phrase “comprising” or the like is used to maintain the “open-end” claims herein, according to traditional claim interpretation. Thus, unless the context requires otherwise, it should be understood that the term “comprise” or variations such as “comprises” or “comprising” or the like, are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency-of this application including any subsequent continuation, division, or continuation-in-part application thereof or any reissue or extension thereon.

What is claimed is:

1. A method of automated sample processing comprising the steps of:

establishing a network including at least one stainer, the at least one stainer having an automated process operation capability that causes automated process operation events through movement of a robotic member;

receiving a protocol in the at least one stainer via the network;

scheduling a plurality of sample process operations based on the protocol;

monitoring operationally-influential exteriorly-consequential information;

automatically processing at least one sample arranged on a first slide using the at least one stainer at least in part through operation of said robotic member sequencing through said scheduled plurality of sample process operations, wherein automatically processing includes dispensing of a buffering agent by the robotic member;

inserting a second slide into the at least one stainer, wherein inserting the second slide does not interfere with movement of the robotic member related to the first slide: and communicating via the network at least some exteriorly-consequential information in response to said step of monitoring operationally-influential exteriorly-consequential information.

2. The method of automated sample processing of claim 1, wherein the at least one stainer includes at least one reagent container, and wherein said step of monitoring usage information comprises the step of monitoring usage of reagent.

3. The method of automated sample processing of claim 2, further comprising the step of automatically communicating via the network a need for replenishing reagent of the at least one reagent container.

4. The method of automated sample processing of claim 1, wherein said step of monitoring operationally-influential exteriorly-consequential information comprises the step of monitoring predictive usage information.

5. The method of automated sample processing of claim 4, wherein said step of monitoring predictive usage information comprises the step of utilizing order lead time information, utilizing reagent order lead time information, or utilizing maintenance lead time information.

6. The method of automated sample processing of claim 1, wherein said step of communicating via the network at least some exteriorly-consequential information comprises the step of automatically informing at least one operator, an administrator, one supplier or one manufacturer of at least some exteriorly-consequential information.

7. The method of automated sample processing of claim 1, further comprising:

receiving a second protocol for processing the second slide in the at least one stainer via the network; and scheduling a second plurality of sample process operations based on the second protocol, wherein communicating via the network at least some exteriorly-consequential information includes communicating via the network information of the insertion of the second slide and of a need for replenishing reagent of the at least one reagent container.

8. The method of automated sample processing of claim 7, further comprising inserting at least one new reagent container into the at least one stainer, where inserting the at least one new reagent container does not interfere with the fluid dispensing of the robotic member.

9. A method of automated sample processing comprising the steps of:

establishing a network including at least one stainer, the at least one stainer having an automated process operation capability that causes automated process operation events through movement of a robotic member;

receiving a protocol in the at least one of stainer via the network;

scheduling a plurality of sample process operations based on the protocol;

processing at least one biological sample arranged on a first slide at least in part through operation of said robotic member sequencing through said scheduled plurality of sample process operations, wherein processing includes dispensing of a buffering agent via the robotic member;

inserting a second slide into the at least one stainer, wherein inserting the second slide does not interfere with movement of the robotic member related to the first slide;

storing details of a number of said plurality of sample process operations as the sample process operations occur;

and receiving an instruction from a user to establish a connection between said network and a remote location, and to display at least a portion of said details at said remote location.

10. A method as described in claim 9, wherein said network is connected to a laboratory network or a laboratory information system.

11. A method as described in claim 9, wherein said connection is established from the network to a remote location that is a manufacturer, supplier, or maintenance personnel location.

12. A method as described in claim 9, wherein storing details of a number of said plurality of sample process operations as the sample process operations occur further comprises storing slide status or processing sequence protocol.

13. An automated sample processing system comprising:

a control system configured to receive a protocol via a network, said control system being configured to at least partially process at least one biological sample arranged on a first slide, and further configured to receive and process a second slide;

a robotic motion system responsive to said control system configured to move a robotic member and to dispense fluids from the robotic member, wherein receiving the second slide does not interrupt fluid dispensing of the robotic member, and wherein dispensing fluids includes dispensing a buffering agent;

a multiple event scheduler configured to schedule a plurality of sample process operations based on the protocol, said robotic motion system being at least in part responsive to the multiple event scheduler;

an operationally-influential exteriorly-consequential information monitor configured to monitor usage information of the sample processing system;

and an exteriorly-consequential information notice element responsive to said operationally-influential exteriorly-consequential information monitor, said exteriorly-consequential information notice element configured to communicate via the network the operationally-influential exteriorly-consequential information.

14. The automated sample processing system of claim 13, further comprising a historical usage information monitor, wherein the stainer also includes at least one reagent container.

15. The automated sample processing system of claim 14, further comprising an automatic predictive need notice element that determines a need for replenishing reagent of the at least one reagent container.

16. The automated sample processing system of claim 15, wherein said operationally-influential exteriorly-consequential information monitor comprises a predictive usage information element.

17. The automated sample processing system of claim 16, wherein said predictive usage information element comprises an order lead time information data element, a reagent order lead time information data element, or a maintenance lead time information data element.

18. The automated sample processing system of claim 17, wherein said exteriorly-consequential information notice element comprises an automatic operator exteriorly-consequential information notice element, an automatic administrator exteriorly-consequential information notice element, an automatic supplier exteriorly- consequential information notice element, or an automatic manufacturer exteriorly-consequential information notice element.

19. The automated sample processing system of claim 13, wherein the control system is further configured to receive a second protocol via the network;

the multiple event scheduler is further configured to schedule a second plurality of sample process operations based on the second protocol, and the exteriorly-consequential information notice element is configured to communicate via the network information regarding the insertion of the second slide and of a need for replenishing reagent of the at least one reagent container.

20. The automated sample processing system of claim 19, wherein the control system is further configured to receive at least one new reagent container, and wherein receiving the at least one new reagent container does not interrupt fluid dispensing of the robotic member.

* * * * *

UNITED STATES PATENT AND TRADEMARK OFFICE
CERTIFICATE OF CORRECTION

PATENT NO. : 8,788,217 B2
APPLICATION NO. : 13/747949
DATED : July 22, 2014
INVENTOR(S) : Gordon Feingold et al.

It is certified that error appears in the above-identified patent and that said Letters Patent is hereby corrected as shown below:

In the Claims:

Claim 1, col. 26, line 5,
"slide: and" should read
--slide; and--.

Claim 18, col. 28, line 23,
"exteriorly- consequential information" should read
--exteriorly-consequential information--.

Signed and Sealed this
Seventeenth Day of March, 2015

Michelle K. Lee
*Director of the United States Patent and Trademark Office*